United States Patent [19]

Pecar et al.

[11] Patent Number: 5,231,216
[45] Date of Patent: Jul. 27, 1993

[54] TRANS-2-ACYLAMINOCYCLOHEXYLOX-YACYLDIPEPTIDES IN THE FORM OF MIXTURES OF DIASTEREOISOMERS THEREOF AND IN THE FORM OF PURE DIASTEREDISOMERS, PROCESS FOR THE PREPARATION THEREOF AND PHARMACEUTICAL COMPOSITIONS CONTAINING THE SAME

[75] Inventors: Slavko Pečar, Domžale; Danijel Kikelj; Uroš Urleb, both of Ljubljana; Marija Sollner, Borovnica; Gašper Marc, Vipava; Aleš Krbavčič, Ljubljana; Vlado Kotnik, Ljubljana; Branka Wraber-Herzog, Ljubljana; Saša Simčič, Ljubljana; Alojz Than, Ljubljana; Lidija Klamfer, Ljubljana; Lučka Povšič, Ljubljana; Zdravko Kopitar, Mengeš; Anton Štalc, Ljubljana, all of Yugoslavia

[73] Assignee: Univerza Edvarda Kardelja v Ljubljana, Ljubljana, Yugoslavia

[21] Appl. No.: 743,233

[22] Filed: Aug. 19, 1991

[30] Foreign Application Priority Data

Aug. 9, 1990 [YU] Yugoslavia .................. 1546/90

[51] Int. Cl.$^5$ ..... C07C 205/00; C07C 233/00/303/00; A01N 37/02
[52] U.S. Cl. ...................... 560/39; 560/125; 562/507; 562/508; 564/17; 564/27; 564/48; 564/53; 564/54; 564/57; 564/80; 564/84; 564/153
[58] Field of Search .............. 562/507, 508; 560/125, 560/39; 564/51, 57, 17, 27, 48, 54, 80, 84, 153; 514/19, 529, 562, 563

[56] References Cited

FOREIGN PATENT DOCUMENTS 3634013 4/1988 Fed. Rep. of Germany ........ 560/39

OTHER PUBLICATIONS

Azuma et al, "Adjuvant Activity of Carbohydrate Analogs of N-Acetylmuramyl-L-Alanyl-D-Isoglutamine on the Induction of Delayed-Type Hypersensitivity to Azobenzeneearsonate-N-Acetyl-L-Tyrosine in Guinea Pigs", *Infection and Immunity*, 33(3) pp. 834–839, Sep. 1981.

March, *Advanced Organic Chemistry*, third edition, pp. 371–373.

Primary Examiner—José G. Dees
Assistant Examiner—Keith MacMillan
Attorney, Agent, or Firm—Pollock, Vande Sande & Priddy

[57] ABSTRACT

There are described novel trans-2-acylaminocyclohexyloxyacyldipeptides of formula I

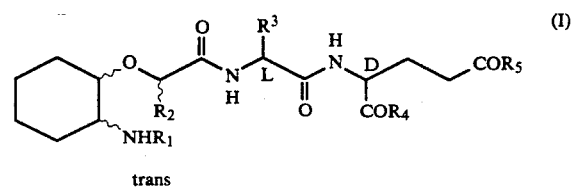

trans wherein
$R_1$ represents $-CO-R_6$, $-SO_2-R_7$ or

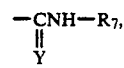

$R_6$ is $C_1-C_{18}$ alkyl or $C_1-C_{18}$ alkoxy,
$R_7$ is $C_1-C_{18}$ alkyl or an optionally substituted phenyl group,
Y is $=O$, $=S$ or $=NH$;
$R_2=R_3$ and represent $-H$ or $C_1-C_{12}$ alkyl,
$R_4$ represents $-OR_8$ or $-NHR_9$,
$R_8$ is $-H$, $C_1-C_8$ alkyl or benzyl,
$R_9$ is $-H$, a straight or branched chain $C_1-C_{18}$ alkyl group or benzyl group;
$R_5$ represents $-OR_9$ or $-NHR_9$,
and novel (1R,2R)- and (1S,2S)-trans-2-acylaminocyclohexyloxyacetyldipeptides of the formulas Ia and Ib (Abstract continued on next page.)

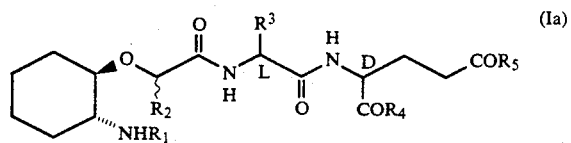 (Ia)

or

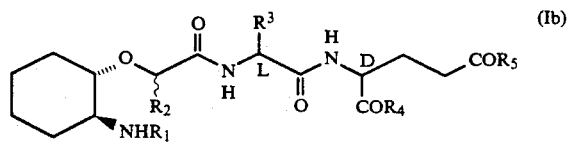 (Ib)

wherein
$R_1$ is $-CO-R_6$, $R_6$ is $C_1-C_{18}$ alkyl,
$R_2$ is $-H$,
$R_3$ is $-H$ or $C_1-C_{12}$ alkyl,
$R_4$ is $-OR_8$ or $-NHR_9$,
 $R_8$ is $-H$, $C_1-C_8$ alkyl or benzyl,
 $R_9$ is $-H$, $C_1-C_{18}$ alkyl or benzyl,
$R_5$ is $-OR_9$ or $-NHR_9$ Compounds of formula I, Ia and Ib and the pharmaceutically acceptable alkali salts thereof show immunomodulatory and antitumour activities and can be used in the preparation of medicaments.

7 Claims, No Drawings

TRANS-2-ACYLAMINOCYCLOHEXYLOXYACYL-DIPEPTIDES IN THE FORM OF MIXTURES OF DIASTEREOISOMERS THEREOF AND IN THE FORM OF PURE DIASTEREDISOMERS, PROCESS FOR THE PREPARATION THEREOF AND PHARMACEUTICAL COMPOSITIONS CONTAINING THE SAME

TECHNICAL FIELD OF THE INVENTION

The invention belongs to the field of pharmaceutical industry and concerns novel trans-2-acylaminocyclohexyloxyacyldipeptides in the form of mixtures of diastereoisomers thereof and in the form of pure diastereoisomers, processes for the preparation thereof and pharmaceutical compositions containing the same. Novel peptides possess an immunomodulatory and antitumoral activity.

TECHNICAL PROBLEM

There exists a continuing need for novel medicaments having strong immunomodulatory and antitumoral activity and as few side effects as possible. Recently, peptides having biological activity have been acquiring increasing significance in this field. Enantiomers or diastereoisomers of the same compound are known as often having different biological effects and the activity of one of the enantiomers or diastereoisomers can be substantially greater than the activity of the other ones. Hence an increasing tendency arises that new therapeutically active substances should be provided in the form of pure enantiomers or diastereoisomers.

PRIOR ART

Muramyl peptides [A. Adam and E. Lederer, in Med. Res. Rev. (1984), 4, 111; G. Baschang, in Tetrahedron (1989), 22, 6331] are components of microbial cell walls having therapeutically interesting effects upon the immunological system. The synthesis of muramyl peptides is a very exacting, multi-stage and expensive one [P. Lefrancier and E. Lederer, in Fortschr. Chemie Org. Naturstoffe (1981), 40, 1].

N-acetylmuramyl-L-alanyl-D-isoglutamine (muramyl dipetide, MDP) is the smallest essential structural element of bacterial cell wall having immunomodulatory activity. However, MDP also has several side effects, e.g. a pronounced pyrogeneous and somnogenous activity, and it can also cause acute arthritis and anaphylactic reaction.

Japanese authors [A. Hasegawa, H. Okumura and M. Kiso, in Gifu Diagaku Nagakubu Kenkyu Hokoku, (1979), 42, 169 (Chem. Abstr., (1980) 93, 239878)] have described muramyl dipeptide derivatives having N-acetylglucosamine substituted by cyclohexanol or a 2,6-dihydroxyaminocyclohexane system and the bioactivity thereof.

In German patent DE 3 634 013 and in the article by D. H. R. Barton et al. in J. Org. Chem. (1989) 54, 3764, there are described the synthesis and the immunostimulatory activity of muramyl dipeptide, wherein the N-acetyl-glucosamine moiety of muramyl dipeptide is substituted by 5-O-substited 2,4,5,6-tetrahydroxy-N-acetylcyclohexylamine.

DESCRIPTION OF THE SOLUTION TO THE TECHNICAL PROBLEM WITH EXAMPLES

The invention concerns novel trans-2-acylaminocyclohexyloxyacyldipeptides of formula I

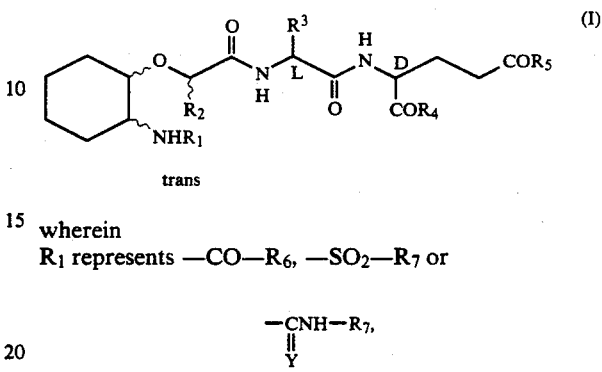

trans wherein
$R_1$ represents —CO—$R_6$, —$SO_2$—$R_7$ or $$-\underset{Y}{\overset{\|}{C}}NH-R_7,$$

wherein
$R_6$ is a straight or branched chain $C_1$-$C_{18}$ alkyl group or a $C_1$-$C_{18}$ alkoxy group,
$R_7$ is a straight or branched chain $C_1$-$C_{18}$ alkyl group, a phenyl group or a phenyl group substituted by a straight or branched chain lower $C_1$-$C_6$ alkyl group or halogen,
Y is =O, =S or =NH;
$R_2$ and $R_3$, which are identical, represent —H or a straight or branched chain $C_1$-$C_{12}$ alkyl group;
$R_4$ represents —$OR_8$ or —$NHR_9$, wherein
$R_8$ is —H, a straight or branched chain $C_1$-$C_8$ alkyl group or benzyl group,
$R_9$ is —H, a straight or branched chain $C_1$-$C_{18}$ alkyl group or benzyl group;
$R_5$ represents —$OR_9$ or —$NHR_9$;
pharmaceutically acceptable alkali salts thereof having immunomodulatory and antitumoral activity, and pharmaceutical compositions containing the same. Further, the invention concerns novel (1R,2R)-trans-2-acylaminocyclohexyloxyacetyldipeptides of the formula Ia (Ia)

and novel (1S,2S)-trans-2-acylaminocyclohexyloxyacetyldipeptides of the formula Ib (Ib)

wherein
$R_1$ represents —CO—$R_6$, wherein $R_6$ is a straight or branched chain $C_1$-$C_{18}$ alkyl group;
$R_2$ represents hydrogen;
$R_3$ represents —H or a straight or branched chain $C_1$-$C_{12}$ alkyl group;
$R_4$ represents —$OR_8$ or —$NHR_9$, wherein $R_8$ is —H, a straight or branched chain $C_1$–$C_8$ alkyl group or benzyl group, $R_9$ is —H, a straight or branched chain $C_1$–$C_{18}$ alkyl group or benzyl group;

$R_5$ represents —$OR_9$ or —$NHR_9$;

pharmaceutically acceptable alkali salts thereof having immunomodulatory and antitumoral activity, and pharmaceutical compositions containing the same.

The invention also concerns a process for the preparation of trans-2-acylaminocyclohexyloxyacyldipeptides of the formula (I), which is considerably shorter, simpler and more economical if compared with the exacting muramyl dipeptide syntheses known from the literature.

Novel compounds of the formula (I) are prepared by reacting trans-2-(2'-acylaminocyclohexyloxy) carboxylic acids of the formula II

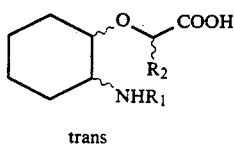

trans wherein $R_1$ and $R_2$ have the same meaning as in formula (I), with dipeptides of formula III

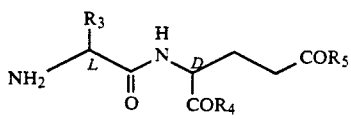

wherein $R_3$, $R_4$ and $R_5$ have the same meaning as in formula I. When $R_4$ and/or $R_5$ are —$OCH_2Ph$, they can have the meaning of a protecting group, which can be removed by hydrogenation. The hydrogenation is carried out in polar solvents such as methanol or acetic acid, at normal or increased pressure and at room temperature. Pd/C is used as the catalyst.

The reaction of trans-2-(2'-acylaminocyclohexyloxy) carboxylic acids of the formula II with dipeptides of formula III to trans-2-acylaminocyclohexyloxyacyldipeptides of formula I is carried out in polar aprotic solvents such as dimethyl formamide, tetrahydrofuran or 1,4-dioxan at a temperature from −10° C. to 25° C., using common reagents for the formulation of the peptide bond such as diphenyl phosphoryl azide, chloroformates or dicyclohexylcarbodiimide.

The compounds of formula I are obtained as mixtures of diastereoisomers, which can be separated by column chromatography as described hereinafter.

The starting trans-2-(2'-acylaminocyclohexyloxy) carboxylic acids of formula II are prepared from morpholine-3-ones of formula IV in the manner shown in the following scheme:

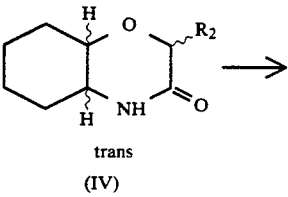

trans
(IV)

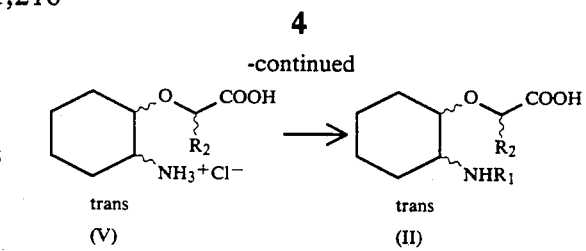

$R_1$ and $R_2$ have the same meaning as in formula I.

Morpholine-3-ones of formula IV are known compounds, which are described in the literature. The preparation thereof is described by M. Gruevski et al. in Synth. Commun. (1989), 19, 2665. They can also be prepared from trans-2-aminocyclohexanol according to the general method for the preparation of morpholine-3-ones as described in EP 61 899 and in the article by Nicoloides et al. in J. Med. Chem. (1986), 29, 259.

Subsequently, morpholine-3-ones are, by acid hydrolysis, e.g. with an aqueous HCl solution at reflux temperature, converted to trans-2-(2'-aminocyclohexyloxy) carboxylic acid hydrochlorides of formula V, which are then, according to known methods, converted to trans-2-(2'-acylaminocyclohexyloxy) carboxylic acids of formula II.

The invention also relates to a process for the preparation of (1R,2R)-trans-2-acylaminocyclohexyloxyacetyldipeptides of formula Ia and (1S,2S)-trans-2-acylaminocyclohexyloxyacetyldipeptides of formula Ib.

The novel compounds of formulas Ia and Ib respectively are prepared by reacting (1'R,2'R)-trans-2-(2'-acylaminocyclohexyloxy) acetic acid of formula IIa

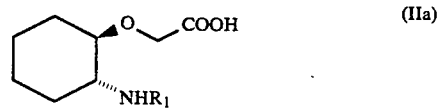

or (1's,2'S)-trans-2-(2'-acylaminocyclohexyloxy) acetic acid of formula IIb

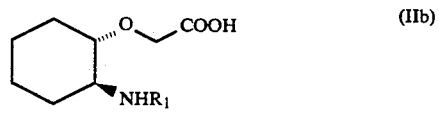

wherein $R_1$ has the same meaning as in formulas Ia and Ib, with dipeptides of formula III

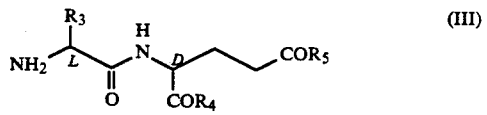

wherein $R_3$, $R_4$, and $R_5$ have the same meaning as in formulas Ia and Ib. When $R_4$ and/or $R_5$ are —$OCH_2Ph$, they can have the meaning of a protecting group, which can be removed by hydrogenation. Hydrogenation is carried out in polar solvents such as methanol or acetic acid at normal or increased pressure. Pd/C is used as the catalyst.

The reaction (1'R,2'R)-trans-2-(2'-acylaminocyclohexyloxy) acetic acid of formula IIa and (1'S,2'S)-trans-2-(2'-acylaminocyclohexyloxy) acetic acid of formula IIb respectively with dipetides of formula III to give (1R,2R)-trans-2-acylaminocyclohexyloxyacetyldipeptides of formula Ia and (1S,2S)-trans-2-acylaminocyclohexyloxyacetyldipeptides of formula Ib respectively is carried out in polar aprotic solvents such as dimethylformamide, tetrahydrofuran or 1,4-dioxan at a temperature from −10° C. to 25° C., using common reagents for the formation of the peptide bond such as diphenyl phosphoryl azide, chloroformates or N,N-dicyclohexylcarbodiimide.

Dipetides of formula III are either known compounds, which are described in the literature [e.g. E. Lefrancier et al., in Bull. Soc. Chim. Biol. 49, 1257 (1967); S. Kusumoto et al., in Bull. Chem. Soc. Jap. 49, 553 (1976)] or can be prepared according to known analogous processes.

(1′R,2′R)-trans-2-(2′-acylaminocyclohexyloxy) acetic acids of formula IIa are prepared from (1R,2R)-trans-2-aminocyclohexanol of formula VIIa in the manner shown in Scheme 1 (for the case that $R_1=COCH_3$, $R_3=CH_3$, $R_4=NH_2$, OH or $OCH_2Ph$, $R_5=OH$ or $OCH_2Ph$). The acylation of (1R,2R)-trans-2-carboxymethoxycyclohexyl ammonium chloride of formula Va is carried out with appropriate carboxylic acid anhydrides or chlorides according to known methods.

(1′S,2′S)-trans-2-(2′-acylaminocyclohexyloxy) acetic acids of formula IIb are prepared from (1S,2S)-trans-2-aminocyclohexanol of formula VIIb in the manner shown in Scheme 2 (for the case that $R_1=COCH_3$, $R_3=CH_3$, $R_4=NH_2$, OH or $OCH_2Ph$, $R_5=OH$ or $OCH_2Ph$). The acylation of (1S,2S)-trans-2-carboxymethoxycyclohexyl ammonium chloride of formula Vb is carried out with appropriate carboxylic acid anhydrides or chlorides according to known methods.

(1R,2R)-trans-2-aminocyclohexanol and (1S,2S)-trans-2-aminocyclohexanol are known compounds. The preparation thereof is described by H. Hoenig et al. in Tetrahedron Lett. 29, 1903 (1988).

Peptides of formulas Ia and Ib respectively are also prepared by chromatographic separation on a silica gel column of a diastereoisomeric mixture of a dipeptide of formula VI

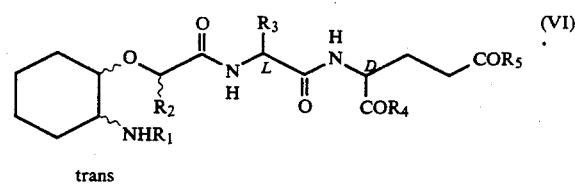

trans which is protected by one or more benzyl groups and wherein the groups $R_1$, $R_2$, $R_3$, $R_4$, and $R_5$, have the same meaning as in above formulas Ia and Ib, with the proviso that at least one of the groups $R_4$ and $R_5$ contains an —$OCH_2Ph$ group.

Mixtures of lower alcohols with halogenated hydrocarbons, e.g. chloroform, dichloromethane or carbon tetrachloride can be used as the mobile phase. After chromatographic separation of diastereoisomers, benzyl groups are removed by hydrogenation as described above, thus yielding (1R,2R)-trans-2-acylaminocyclohexyloxyacetyldipeptides of formula Ia and (1S,2S)-trans-2-acylaminocyclohexyloxyacetyldipeptides of formula Ib respectively.

Schemes 1 and 2 show the reaction sequence for the synthesis of compounds of formula Ia and Ib respectively, whose preparation is explained in the Examples. Scheme 1 shows the reaction scheme for the preparation of compounds having R,R configuration and Scheme 2 shows the reaction scheme for the preparation of compounds having S,S configuration on the asymmetrical centres of cyclohexane ring.

SCHEME 1

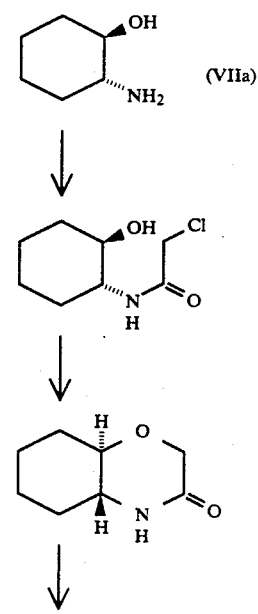

-continued
SCHEME 1
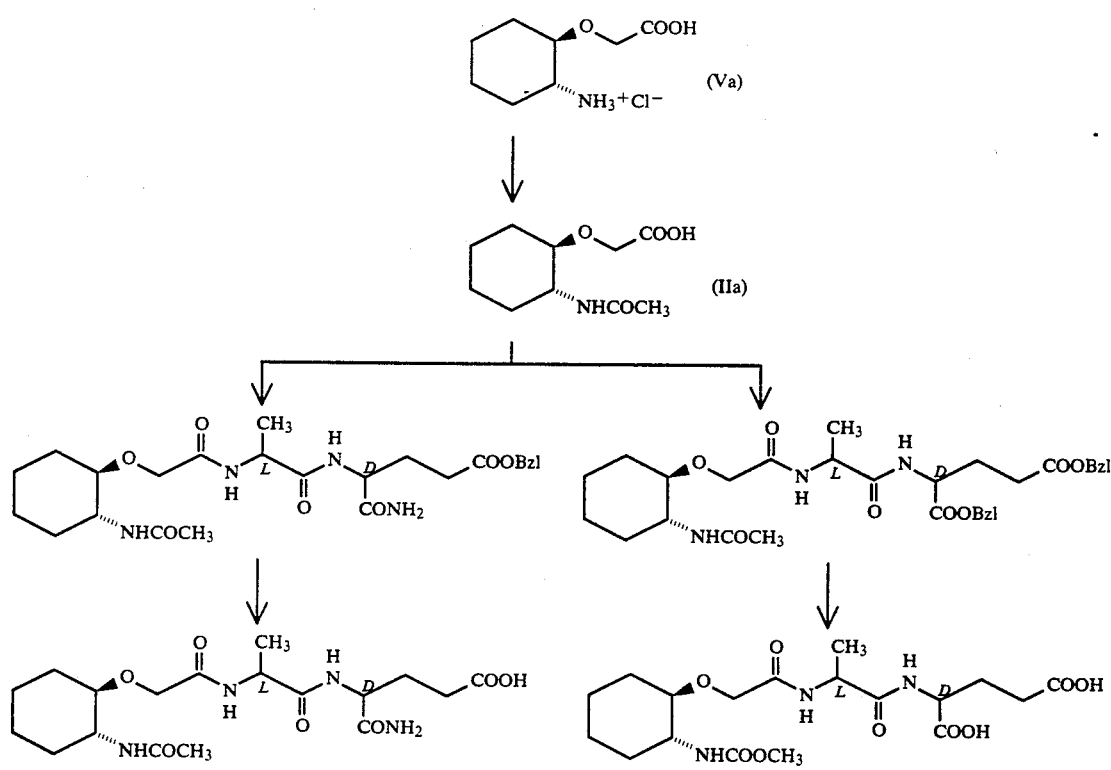
Note: Bzl = —CH₂Ph
SCHEME 2
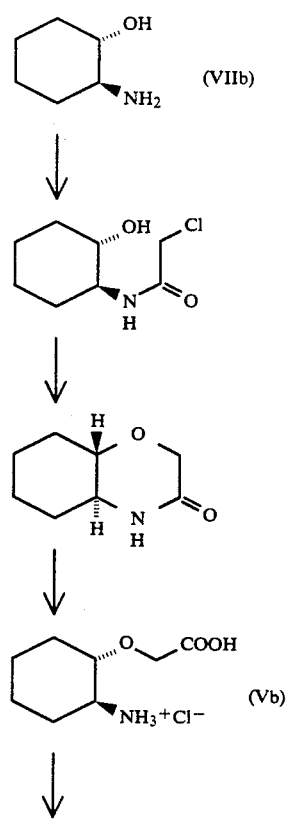

-continued
SCHEME 2

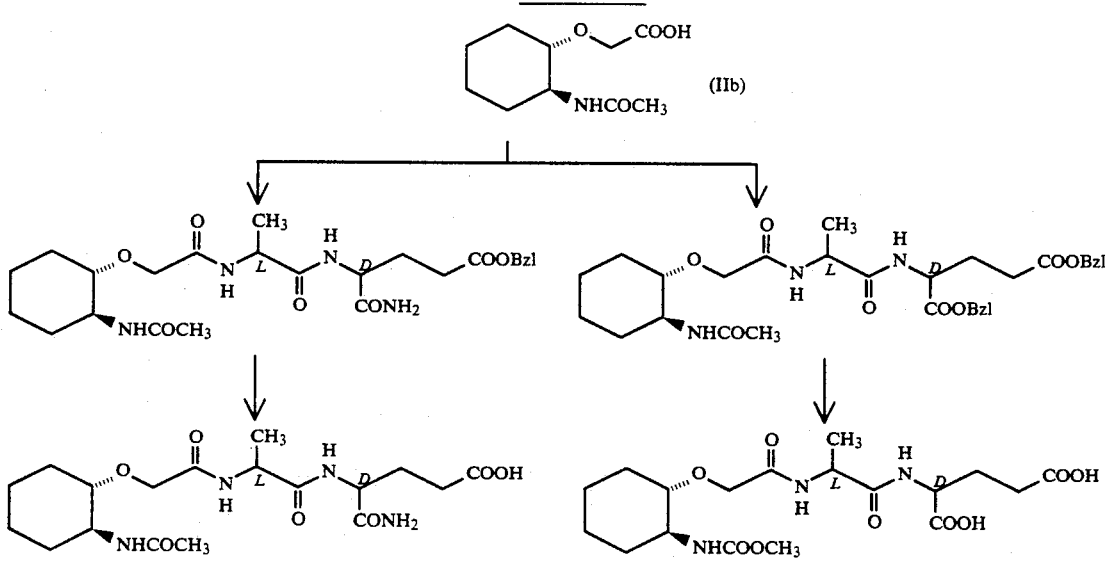

Note: Bzl = —CH₂Ph

BIOLOGICAL STUDIES

The following tests were performed:
1. Immunological tests
   1.1 Determination of the number of lymphocytes B and lymphocytes T
   1.2 Determination of the number of macrophages
   1.3 Blast transformation of lymphocytes by mithogens
   1.4 Activation of peritoneal macrophages
   1.5 Determination of haemolytic plaques for the assessment of the maturation of lymphocytes B
2. Antitumour activity
3. Pyrogenous activity
4. Toxicity Immunological studies were performed on female HAN-NmRI strain mice of 3-4 weeks, weighing from 17-20 g.

In tests 1.1 to 1.5, the animals were first administered the Brewer's thioglycolate medium by i.p. injection, which was followed after 6 hours by the injection of 0.5 ml of a solution containing 25 µg, 2.5 µg and 0.25 µg respectively of N-acetyl-muramyl-L-alanyl-D-isoglutamine (muramyl dipeptide, MDP) or of N-[trans-2-(2'-acetylaminocyclohexyloxy)acetyl]-L-alanyl-D-glutaminic acid (compound 1, Example 12B). Equal doses were administered to the animals on days 2 and 3. On day 4 the animals were sacrificed and the spleen and the peritoneal macrophages were isolated.

1.1 Determination of the Number of Lymphocytes B and Lymphocytes T

To the isolated splenic lymphocytes there were added fluorescein isothiocyanate labelled antimouse antibodies (for the determination of lymphocytes B) and anti-Thy 1 monoclonal antibodies (for the determination of lymphocytes T) respectively. After incubation and rinsing with RPMI 1640 medium (Gibco, Great Britain), the lymphocytes were counted by fluorescence microscopy.

Neither the number of splenic lymphocites B nor of lymphocytes T was altered to a statistically significant extent either by muramyl dipeptide or by a compound 1.

1.2 Determination of the Number of Macrophages

The number of macrophages in the peritoneal cavity washings was determined three days after the stimulation with Brewer's thioglycolate medium. The cells were suspended in ice-cold RPMI 1640 medium, to which trypan blue was added, and counted in Neubauer's chamber.

The number of peritoneal macrophages was not altered to a statistically significant extent either by muramyl dipeptide or by compound 1.

1.3 Blast Transformation of Lymphocytes by Mithogens

Isolated splenic lymphocytes were prepared in a concentration of $1 \times 10^6$/ml in the RPMI 1640 medium, to which there were added 10% of foetal calf serum (FCS) (Sera-Lab, Great Britain), 1 ml of 200 mM L-glutamine solution and 1 ml of an antibiotic solution (100 U/ml of penicillin and 100 µg/ml of streptomycin) for 100 ml of complete medium. To each flat bottom well of a microtitration plate (T grade, Nunc, Denmark) 100 µl of the cell suspension were distributed. The cells were stimulated in vitro by adding concanavalin A (con A)(Pharmacia, Sweden) at respective concentrations of 16, 8, and 4 µg/ml. Control lymphocyte cultures were grown in basal medium only. The cells were then incubated at 37° C., 5% CO₂ and 95% humidity for 2 days, followed by the addition of tritium labelled thymidine. After 16 hours the samples were prepared for the measurement in a β-counter. The results were expressed as incorporation indexes with respect to the control group of the animals.

Studies of concanavalin A influence on the blast transformation ability showed that muramyl dipeptide did not affect the blastic activity of lymphocytes T, whereas the compound 1 in the doses of 25 µg increased this activity for about 150% (p<0.05). The results indicated a dose-dependent effect.

TABLE 1

In vivo immunomodulatory effect of muramyl dipeptide (MDP) and of compound 1 on the blast transformation ability of lymphocytes, stimulated in vitro with concanavalin A

| Substance | Daily dose (µg)* | Amount of active thymidine incoporated in lymphocyte DNA (cpm) $\bar{x}$ + s.e.m (n) | p |
|---|---|---|---|
| MDP | 25 | 7460 ± 1980 (5) | >0.05 |
| | 2.5 | 12440 ± 3540 (5) | >0.05 |
| | 0.25 | 19840 ± 9400 (5) | >0.05 |
| Compound 1 | 25 | 25990 ± 7850 (5) | <0.05 |
| | 2.5 | 16830 ± 6610 (5) | >0.05 |
| | 0.25 | 10780 ± 2680 (5) | >0.05 |
| Control | | 10130 ± 476 (5) | — |

*Said doses were administered to the animals for 3 consecutive days.

When compared with MDP, compound 1 showed a statistically greater (p<0.05) immunomodulatory effect in lymphocytes T at the dose of 25 µg.

1.4 Activation of Peritoneal Macrophages

The peritoneal cavity of the animals was rinsed with 4 ml of ice-cold RPMI 1640 medium. The cytolysis of erythrocytes was effected with 0.2% NaCl. The remaining cells were washed twice in a cooled centrifuge at 4° and 1500 rpm for 5 minutes with ice-cold RPMI 1640 medium. The cells were re-suspended and the concentration was adjusted to $1.5 \times 10^6$/ml. The cell suspension was distributed among the flat bottom wells of a microtitration palte (T grade, Nunc, Denmark). After incubating for 2 hours at 37° C., 5% $CO_2$ and 95% humidity, the wells were rinsed with warm RPMI 1640 medium and the adhering macrophages were used for testing.

The macrophages were covered with 100 µl of a 160 µM ferricytochrome C solution in HBSS (Hank's Balanced Salt Solution) without phenol red or with 100 µl of ferricytochrome C in a 200 nM phorbol miristate acetate (PMA, Sigma, St. Louis, U.S.A.) solution or with 100 µl of ferricytochrome C, PMA amd 240 units/ml of superoxide dismutase (SOD, Sigma, St. Louis, U.S.A.), which specifically inhibits the reduction of cytochrome C with the superoxide ion (blank) respectively. After incubating for 90 minutes at 37° C., 5% $CO_2$ and 95% humidity, the absorbance was measured at the wavelength of 570 nm.

The results are shown in Table 2 as the difference in the absorbance of the test sample and of the blank, calculated for 1 mg of cell protein.

In the studies of macrophage activation it was shown that muramyl dipeptide increased the activity at all three doses by about 120% (p<0.001), whereas the compound 1 increased the activity at the dose of 2.5 µg by 55% (p<0.06) and at the dose of 25 µg by 70% (p<0.05). For the compound 1 the effects were dose-dependent.

As shown in Table 3, similar results were found after additional macrophage activation with PMA. In this case muramyl dipeptide at all doses increased the activity by about 150% (p<0.001) and compound 1 increased the activity at the dose of 2.5 µg by 50% (p<0.05) and at the dose of 25 µg by 70%. In this case the results were dose-dependent as well.

In either test at the dose of 25 µg there was no statistically significant different (p=0.05) between the respective macrophage activation achieved by muramyl dipeptide and by compound 1.

TABLE 2

In vivo immunomodulatory effect of muramyl dipeptide (MDP) and of compound 1 upon macrophage activation without additional in vitro stimulation with phorbol miristate acetate (PMA)

| Substance | Daily dose (µg)* | Difference in absorbancies of the test sample and of the blank per mg of cell protein $\bar{x}$ + s.e.m (n) | p |
|---|---|---|---|
| MDP | 25 | 578 ± 81 (5) | <0.01 |
| | 2.5 | 578 ± 42 (5) | <0.001 |
| | 0.25 | 614 ± 35 (5) | <0.001 |
| Compound 1 | 25 | 489 ± 97 (5) | <0.05 |
| | 2.5 | 431 ± 85 (5) | <0.06 |
| | 0.25 | 237 ± 94 (5) | >0.05 |
| Control | | 275 ± 26 (5) | — |

TABLE 3

In vivo immunomodulatory effect of muramyl dipeptide (MDP) and of compound 1 upon macrophage activation with additional in vitro stimulation with phorbol miristate acetate (PMA)

| Substance | Daily dose (µg)* | Difference in absorbancies of the test sample and of the blank per mg of cell protein $\bar{x}$ + s.e.m (n) | p |
|---|---|---|---|
| MDP | 25 | 2138 ± 165 (5) | <0.001 |
| | 2.5 | 2207 ± 213 (5) | <0.001 |
| | 0.25 | 2657 ± 595 (5) | <0.05 |
| Compound 1 | 25 | 1709 ± 374 (5) | <0.05 |
| | 2.5 | 1494 ± 199 (5) | <0.05 |
| | 0.25 | 1298 ± 334 (5) | >0.05 |
| Control | | 1004 ± 38 (5) | — |

*Said doses were administered to the animals for 3 consecutive days.

1.5 Determination of Haemolytic Plaques for the Assessment of the Maturation of Lymphocytes B A 1% suspension of sheep erythrocytes (Institute of Microbiology, Faculty of Medicine, Ljubljana, Yugoslavia) in physiological saline was used for the immunisation. First, individual mice were administered 0.2 ml of this suspension by i.p. injection, followed next day by 0.1 ml (1 µg/mouse) of the test substance. The immunisation was completed on the fifth day after the administration of sheep erythrocytes and the mice were sacrificed.

Their spleens were removed and homogenized in Parker 199 Medium with added aminoacids, streptomycin and sodium carbonate (Torlak, Beograd, Yugoslavia). The lymphocytes were separated on the Ficol Separating Medium (Pharmacia, Uppsala, Sweden). After repeated rinsing with Parker 199 Medium, the cells were resuspended in RPMI 1640 nutrient medium with added 10% of foetal calf serum and streptomycin. To 50 µl of the cell suspension, 450 µl of trypan blue were added and the cells were counted in Neubauer's chamber. The number of lymphocytes per ml of the cell suspension was calculated. To 100 µl of the diluted cell suspension there were added 200 µl of RPMI 1640 nutrient medium, 50 µl of a 10% suspension of sheep erythrocytes and 50 µl of guinea pig complement (Institute of Microbiology, Faculty of Medicine, Ljubljana, Yugoslavia). The reaction mixture (RM) was put into the prepared chambers on the slide, the chambers were sealed with white wax and incubated at 37° C. for 60 minutes. After the completion of the incubation, the plaques were counted under microscope.

The number of plaques per $1 \times 10^6$ cells was calculated according to the following equations:

Number of plaques =

$$\frac{1 \times 10^6 \text{ cells} \times \text{number of plaques per chamber}}{A \text{ cells/chamber}}$$

$A$ cells per chamber =

$$\frac{\text{amount of } RM \text{ per chamber } (\mu l) \times \text{number of cells in } RM}{\text{amount of } RM \, (\mu l)}$$

At a dose of 1 μg/mouse, the substance caused a significant increase (p<0.001) of the number of plaques from 136.2±17.0 (n=12) to 331.6±25.3 (n=13). The values were reported as x̄±s.e.m. (n=number of samples).

2. Antitumour Activity

The studies were performed on A/J strain mice (Institute Rudjer Bošković, Zagreb, Yugoslavia) of 8 to 10 weeks. All animals used in the same experiment were of the same sex and age.

Fibrosarcoma SA-1 was used as the experimental tumour model. Tumorous cells were obtained from the ascitic form of the SA-1 tumour of the syngeneic A/J mouse. They were implanted into animals dorsilaterally by s.c. injection of $5 \times 10^5$ tumour cells. The testing was started after the tumours had grown to a volume of 35 mm³. The test substance was injected i.p. on five consecutive days in a dose of 2.5 or 25 μg. The growth of the tumours was monitored by measuring the diameters and the thickness of the tumours. The tumour volumes were calculated according to the formula $0.523 \times a \times b \times c$ (a, b and c being the tumour diameters).

The delay in the growth of each individual tumour was obtained by deducting the relevant time of growth of the tumour in the control group from the time needed for the growth of the tumour to reach the volume of 150 mm³.

In comparison to the control, the antitumour activity of the compound 1 was moderate and statistically significant at the dose of 25 μg (p<0.002). However, there was no statistically significant difference in activity between the higher and the lower dose.

An increased delay in tumour growth was also obtained by combining the compound 1 (2.5 μg) with the recombinant tumour necrosis factor αN∇3 ($5 \times 10^5$ U). Compound 1 decreased the side effects of the tumour necrosis factor.

TABLE 4

Time needed for the tumour growth to the volume of 150 mm³ and the delay in tumour growth

| Substance | n | Number of days (± SD) | Growth delay (± SD) | p (compared with control) |
|---|---|---|---|---|
| Control | 22 | 5.5 ± 0.8 | | |
| Compound 1 | | | | |
| 2.5 μg* | 12 | 6.4 ± 0.9 | 0.9 ± 0.4 | <0.2 |
| 25.0 μg | 11 | 7.3 ± 1.3 | 1.8 ± 0.4 | <0.002 | n = number of experiments
*daily dose; the animals received 5 doses

3. Pyrogenous Activity

The pyrogenous activity was determined according to the method of USP XXII. In contrast to MDP, compound 1 did not show any pyrogenous activity.

4. Toxicity

The average lethal dose ($LD_{50}$) at i.v. application of the compound 1 in male mice was >500 mg/kg.

Evaluation of Compound 1

Compound 1 is an immunomodulator, which enhances the muturation of lymphocytes B to plasma cells and increases the activity of lymphocytes B and lymphocytes T as well as that of macrophages but does not alter the number of these immunologically competent cells. In the tested range the effect is dose-dependent. As an immunomodulator it also shows an antitumour activity; when combined with the tumour necrosis factor, it increases the activity and decreases the side effects of the latter. In contrast to muramyl dipeptide, which similarly acts upon different immunologically competent cells, compound 1 is neither pyrogenous nor very toxic.

PHARMACEUTICAL PREPARATIONS

The pharmaceutical preparations of the invention can be in the form of coated pills, tablets, capsules, ampoules or aerosols to be used on mucous membranes. Preparations suitable for parenteral application can also comprise liposomes.

The pharmaceutical preparations of the invention comprise the pharmacologically active compound alone or together with a pharmaceutically acceptable carrier chosen with respect to the mode of application. Pharmaceutical preparations are manufactured according to methods known per se.

The dose, the frequency and the mode of application will depend on various factors such as the intended use (e.g. for the treatment of the primary or secondary immunodeficiency or of various types of infections or for increasing the antitumour activity).

A suitable dose for an adult wil be from 0.1 to 250 mg/day. The exact dose, the frequency and the mode of application will be chosen with respect to the activity and pharmacokinetic properties of the particular compound and to other factors that can affect the effect of the drug, such as the type and severity of the condition, the patient's age, weight, sex and response to the medication.

EXAMPLE

| Lyophilized injections | |
|---|---|
| Compound 1 | 1 mg |
| Manitol | 5 mg |
| Sodium hydroxyde or hydrochloric acid (for pH adjustment) | q.s. |
| Water for injections | 1 ml |

The invention is illustrated by the following non-limiting Examples.

EXAMPLES

Preparation of the Compounds of Formula I

STARTING COMPOUNDS

Example 1

Trans-2-carboxymethoxy-cyclohexyl ammonium chloride

A solution of trans-octahydro-2H-1,4-benzoxazine-3-one (7.75 g, 50 mmoles) in 18% aqueous HCl (240 ml) was refluxed for 4 hours and evaporated in vacuo to a white solid, which was recrystallized from a mixture of ethanol and diethyl ether. Thus, there were obtained 9.85 g (94%) of the title compound, m.p. 194°–196° C.

Analysis for $C_8H_{16}ClNO_3$
calculated: 45.83% C, 7.69% H, 6.68% N.
found: 45.62% C, 7.85% H, 6.73% N.

IR (KBr): 3500–2450 br., 1745 (CO) $cm^{-1}$;

$^1$H-NMR (60 MHz, $D_2O$): $\delta=1.2–2.55$ (m, 8H, 4 $CH_2$), 2.9–3.9 (m, 2H, 1-H, 2-H), 4.4 (s, 2H, $OCH_2$) ppm.

Example 2

Trans-2-(1'-carboxyethoxy)-cyclohexyl ammonium chloride

The compound was prepared from trans-2-methyl-octahydro-2H-1,4-benzoxazine-3-one in a manner analogous to the one described in Example 1.

Yield: 98% theor.
Melting point: 198°–200° C.
Analysis for $C_9H_{18}ClNO_3$:
calculated: 48.32% C, 8.11% H, 6.26% N.
found: 48.46% C, 8.46% H, 6.05% N.

$^1$H-NMR (300 MHz, DMSO-$d_6$): $\delta=1.10$, 1.26 (m, 4H, $4H_{ax}$), 1.34 (d, 3H, J=6.8 Hz, $CH_3$), 1.52–1.73 (m, 2H, $2H_{eq}$), 1.94–2.14 (m, 2H, $2H_{eq}$), 2.80–2.96 (m, 1H, 2'-H), 3.30–3.46 (m, 1H, 1'-H), 4.08 (q, 1H, J=6.8 Hz, CH); 8.11 (s, 3H, $NH_3^+$), 12.56 (s, 1H, COOH) ppm.

Example 3

Trans-2-(2'-acetylaminocyclohexyloxy) acetic acid

To a cooled solution of trans-2-carboxymethoxy-cyclohexyl ammonium chloride (1.048 g, 5 mmoles) in 2N NaOH (5 ml), there were added under stirring first 1N NaOH (1 ml) and then acetic anhydride (0.102 g, 1 mmol). When the reaction of anhydride was completed and a homogeneous solution was obtained, the same amount of 1N NaOH and acetic anhydride as above was added four times. After the addition of the last portion the reaction mixture was stirred for 30 minutes, the solution was acidified to pH 2 and extracted with ethyl acetate (5×20 ml). The organic extracts were dried with $MgSO_4$, the drying agent was filtered off and the filtrate was evaporated under reduced pressure. The residue was recrystallized from a mixture of chloroform/n-hexane. Thus, there were obtained 0.60 g (56%) of the title compound, melting point 141°–143° C.

Analysis for $C_{10}H_{17}NO_4$:
calculated: 55.80% C, 7.96% H, 6.51% N.
found: 55.76% C, 8.25% H, 6.75% N.

IR (KBr): 3305 (NH), 1750 (COOH), 1645, 1560 (CONH) $cm^{-1}$;

MS: calculated 215.25, found 215 (M+); .

$^1$H-NMR (60 MHz, $CDCl_3$): $\delta=0.85–2.65$ (m, 8H, 4 $CH_2$), 2.07 (s, 3H, $CH_3$), 2.8–3.7 (m, 2H, 1'-H, 2'-H), 4.1 (AB-system, 2H, J=18 Hz, $OCH_2$), 8,25 (br.s, 1H, NH), 10.6 (br.s, 1H, COOH) ppm.

Example 4

Trans-2-(2'-acetylaminocyclohexyloxy) propionic acid

The compound was prepared from trans-2-(1'-carboxyethoxy)-cyclohexyl ammonium chloride in a manner analogous to the one described in Example 3.

Yield: 76% theor.
Melting point: 166°–169° C.

$^1$H-NMR (300 MHz, DMSO-$d_6$): $\delta=1.00–1.22$ (m, 4H, $4H_{ax}$), 1.15 (d, 3H, J=6.8 Hz, $CH_3$), 1.49–1.63 (m, 3H, $3H_{eq}$), 1.76 (s, 3H, $CH_3CO$), 1.94–1.98 (m, 1H, $1H_{eq}$), 3.00–3.06 (m, 1H, 2'-H), 3.50–3.53 (m, 1H, 1'-H), 4.03 (q, 1H, CH), 7.69 (d, 1H, NH, J=8.8 Hz), 12.41 (s, 1H, COOH) ppm.

Example 5

Trans-2-(2'-p-toluenesulphonamidocyclohexyloxy) acetic acid

To a solution of trans-2-carboxymethoxy-cyclohexyl ammonium chloride (1.048 g, 5 mmoles) in 1N NaOH (15 ml), there was aded a solution of p-toluenesulphonyl chloride (1.048 g, 5.5 mmoles) in diethyl ether (20 ml). The mixture was vigorously stirred for 20 hours at room temperature. The aqueous phase was separated, washed with diethyl ether (20 ml), acidified with HCl 18% to pH 2 and extracted with diethyl ether (5×20 ml). The organic extracts were dried with $MgSO_4$, the drying agent was filtered off and filtrate was evaporated in vacuo. The residue was recrystallized from diisopropyl ether. Thus, there were obtained 1.09 g (67%) of the title compound in the form of white crystals, melting point 56°–58° C.

Analysis for $C_{15}H_{21}NO_5S$:
calculated: 55.03% C, 6.47% H, 4.28% N.
found: 55.15% C, 6.61% H, 4.03% N.

IR (KBr): 3240 (NH), 1720 (COOH), 1345, 1170, 1160 ($SO_2NH$) $cm^{-1}$;

MS: calculated 327.40, found 327 (M+);

$^1$H-NMR (300 MHz, DMSO-$d_6$) $\delta=0.95–1.20$ (m, 4H, 3',4',5',6'-$H_{ax}$), 1.4–1.55 (m, 2H, 4',5'-$H_{eq}$), 1.80–1.95 (m, 2H, 3',6'-$H_{eq}$), 2.35 (s, 3H, $CH_3$), 2.75–2.85 (m, 1H, 2'-H), 2.98–3.08 (m, 1H, 1'-H), 3.4 (br.s, NH+COOH+$H_2O$), 3.92 (AB-system, 2H, J=17.1 Hz, $OCH_2$), 7.34 (d, 2H, 2"-H, 6"-H), 7.67 (d, 2H, 3"-H, 5"-H) ppm.

Example 6

Trans-2-(2'-p-toluenesulphonamidocyclohexyloxy) propionic acid

The compound was prepared from trans-2-(1'-carboxyethoxy)-cyclohexyl ammonium chloride in a manner analogous to the one described in Example 5.

Melting point: 143°–145° C.
Analysis for $C_{16}H_{23}NO_5S$:
calculated: 56.29% C, 6.79% H, 4.10% N.
found: 56.48% C, 6.98% H, 3.82% N.

Example 7

Trans-2-(2'-methylsulphonylaminocyclohexyloxy) acetic acid

The compound was prepared from trans-2-carboxymethoxy-cyclohexyl ammonium chloride (1.048 g, 5 mmoles) in a manner analogous to the one described in Example 5. Thus, there were obtained 0.38 g (30%) of the title compound, melting point 119°–121° C.

Analysis for $C_9H_{17}NO_5S$:

calculated: 43.01% C, 6.82% H, 5.57% N.
found: 48.28% C, 6.95% H, 5.41% N.
IR (KBr): 3250 (NH), 1735 (COOH), 1355, 1170, 1155 ($SO_2NH$) $cm^{-1}$;
MS: calculated 251.30, found 251 ($M^+$);
$^1$H-NMR (60 MHz, $CDCl_3$): δ=0.83-2.43 (m, 8H, 4 $CH_2$), 2.67-3.43 (m, 2H, 1'-H, 2'-H), 3.0 (s, 3H, $CH_3$), 4.13 (AB-system), 2H, J=18 Hz, $OCH_2$), 6.5 (br.s, 2H, NH, COOH) ppm.

Example 8

Trans-2-(2'-ethylsulphonylaminocyclohexyloxy) acetic acid

The compound was prepared from trans-2-carboxymethoxy-cyclohexyl ammonium chloride (0.964 g, 7.5 mmoles) in a manner analogous to the one described in Example 5. Thus, there were obtained 0.56 g (42% of the title compound, melting point 120°-122° C.

Analysis for $C_{10}H_{19}NO_5S$:
calculated: 45.27% C, 7.22% H, 5.28% N.
found: 45.65% C, 7.47% H, 5.16% N.
IR (KBr): 3310 (NH), 1740 (COOH), 1330, 1305, 1140 ($SO_2NH$) $cm^{-1}$;
MS: calculated 265.33, found 265 ($M^+$);
$^1$H-NMR (60 MHz, $CDCl_3$): δ=0.87-2.4 (m, 8H, 4 $CH_2$), 1.30 (t, 3H, J=7 Hz, $CH_3$), 2.67-3.23 (m, 4H, $SO_2CH_2$, 1'-H, 2'-H), 4.03 (AB-system, 2H, J=18 Hz, $OCH_2$), 5.86 (br.s, 1H, NH), 7.95 (br.s, 1H, COOH) ppm.

Example 9

Trans-2-[2'-(N'-phenylureido)cyclohexyloxy] acetic acid

To a solution of trans-2-carboxymethoxy-cyclohexyl ammonium chloride (0.419 g, 2 mmoles) in 2N NaOH (10 ml), phenylisocyanate (0.476 g, 4 mmoles) was added under stirring. After 1 hour the solution was extracted with diethyl ether (10 ml) and the aqueous phase was acidified with HCl 18% to pH 3. The title compound separated in the form of white crystals, which were filtered off and dried over $P_2O_5$. Thus, there were obtained 0.23 g (40%) of the title compound, melting point 166°-168° C.

Analysis for $C_{15}H_{20}N_2O_4$:
calculated: 61.63% C, 6.90% H, 9.58% N.
found: 61.36% C, 6.96% H, 9.43% N.
IR (KBr): 3350, 3300 (NH), 1740 (COOH), 1640, 1565 (CONH) $cm^{-1}$;
$^1$H-NMR (300 MHz, DMSO-$d_6$): δ=1.1-2.0 (m, 8H, 4 $CH_2$), 3.15-3.25 (m, 1H, 2'-H), 3.4-3.55 (m, 1H, 1'-H); 4.05 (AB-system, 2H, $OCH_2$), 6.3 (br.d, 1H, NH), 6.85 (m, 1H, H-arom.), 6.95 (m, 2H, 2H-arom.), 7.15 (m, 2H, 2 H-arom.), 8.7 (br.s, 1H, NH), 10.4 (br.s, 1H, COOH) ppm.
MS: calculated 292.34, found 292 ($M^+$).

Example 10

Trans-2-[2'-(N'-phenylthioureido)cyclohexyloxy] acetic acid

To a solution of sodium ethoxyde prepared from Na (0.046 g, 2 mmoles) and ethanol (10 ml), there were added trans-2-carboxymethoxy-cyclohexyl ammonium chloride (0.419 g, 2 mmoles) and phenylisothiocyanate (0.270 g, 2 mmoles). The mixture was refluxed for 1 hour, evaporated and the residue was dissolved in 1N NaOH (25 ml). The solution was extracted with diethyl ether (2×20 ml), the aqueous phase was acidified with HCl 18% to pH 2 and reextracted with diethyl ether (3×20 ml). The organic phase was dried with $MgSO_4$, the drying agent was filtered off and the filtrate was evaporated in vacuo. The residue was recrystallized from a mixture of ethanol/ether. Thus, there were obtained 0.185 g (30%) of the title compound in the form of white crystals, melting point 147°-149° C.

Analysis for $C_{15}H_{20}N_2O_3S$:
calculated: 58.42% C, 6.54% H, 9.08% N.
found: 58.63% C, 6.81% H, 9.42% N.
IR (KBr): 3300, 3250 (NH), 1750 (COOH), 1545, 1515 $cm^{-1}$;
MS: calculated 308.4, found 309 ($M^+ + 1$);
$^1$H-NMR (300 MHz, DMSO-$d_6$): δ=1.05-1.40 (m, 4H, 3',4',5',6'-$H_{ax}$), 1.50-1.75 (m, 2H, 4',5'-$H_{eq}$), 2.00-2.12 (m, 2H, 3',6'-$H_{eq}$), 3.35-3.50 (m, 1H, 2'-H), 4.0-4.1 (m, 3H, $OCH_2$, 1'-H), 7.10 (m, 1H, H-arom.), 7.29 (m, 2H, 2H-arom.), 7.39 (m, 2H, H-arom.), 7.81 (br.d, 1H, NH), 9.49 (br.s, 1H, NH), 12.65 (br.s, 1H, COOH) ppm.

Example 11

Trans-2-(2'-t-butyloxycarbonylaminocyclohexyloxy) acetic acid

To a solution of trans-2-carboxymethoxy-cyclohexyl ammonium chloride (0.42 g, 2 mmoles) in dry dioxane, there were added triethylamine (0.61 g, 6 mmoles) and di-tert.-butyldicarbonate (0.52 g, 2.4 mmoles). The mixture was stirred for 6 hours at the temperature of 50° C. and then evaporated in vacuo. The residue was dissolved in water (5 ml), the solution was acidified with 10% citric acid to pH 2 and extracted with ethyl acetate (3×10 ml). The organic phase was dried with $MgSO_4$, the drying agent was filtered off and the filtrate was evaporated. Thus, there were obtained 0.36 g (66%) of the title compound, melting point 205°-207° C.

Analysis for $C_{13}H_{23}NO_5$;
calculated: 57.13% C, 8.48% H, 5.12% N.
found: 57.37% C, 8.71% H, 4.93% N.
IR (KBr): 3380 (NH), 1750 (COOH), 1685, 1540 (NHCOO) $cm^{-1}$;
MS: calculated 273.33, found 273 ($M^+$);
$^1$H-NMR (60 MHz, $CDCl_3$): δ=0.87-2.3 (m, 8H, 4 $CH_2$), 1.47 (s, 9H, 3 $CH_3$), 2.8-3.63 (m, 2H, 1'-H, 2'-H), 4.06 (AB-system, 2H, J=18 Hz, $OCH_2$), 5.20 (br.s, 1H, NH), 7.03 (br.s, 1H, COOH) ppm.

COMPOUNDS OF THE INVENTION

Example 12

A. Dibenzyl N-[trans-2-(2'-acetylaminocyclohexyloxy)acetyl]-L-alanyl-D-glutamate To a solution fo dibenzyl L-alanyl-D-glutamate hydrochloride (869 mg, 2 mmoles) and trans-2-(2'-acetylaminocyclohexyloxy) acetic acid (430 mg, 2 mmoles) in dry dimethylformamide (9 ml), there was added, under stirring on ice bath, diphenylphosphoryl azide (550 mg, 2 mmoles), followed by triethylamine (0.56 ml, 4 mmoles). The stirring was continued for another hour on ice bath and for 60 hours at room temperature. Ethyl acetate (40 ml) was added thereto and the mixture was extracted successively with 10% citric acid (3×5 ml), distilled water (3×5 ml), saturated NaCl solution (3×5 ml), saturated $NaHCO_3$ solution (3×5 ml), distilled water (3×5 ml) and saturated NaCl solution (3×5 ml). The mixture was dried with magnesium sulphate, the drying agent was filtered off and ethyl acetate was removed from the filtrate by distillation, thus obtaining 1.0 g (84%) of the title compound in the form of a pale yellow oil.

¹H-NMR (300 MHz, CDCl₃): δ=1.0-1.38 (m, 4H, 4 H$_{ax}$), 1.38 (1.39)(d, 3H, J=7.0 Hz, CH₃-Ala), 1.60-1.80 (m, 2H, 2H$_{eq}$), 1.90-2.15 (m, 4H, 2 H$_{eq}$, CH₂-βGlu), 1.95 (1.96)(s, 3H, COCH₃), 2.41 (t, 2H, CH₂-γGlu), 3.00-3.10 (m, 1H, 2'-H), 3.70-3.90 (m, 1H, 1'-H), 3.9 (3.99)(AB-system, 2H, J=15.1 Hz, OCH₂), 4.40-4.63 (m, 2H, CH-Glu, CH-Ala), 5.09 (s, 2H, CH₂-benzyl), 5.14 (s, 2H, CH₂-benzyl), 6.15 (6.62)(d, 1H, J=8.0 Hz, NH), 7.20-7.44 (m, 12H, 10H-arom., 2NH) ppm.

B.
N-[Trans-2-(2'-acetylaminocyclohexyloxy)acetyl]-L-alanyl-D-glutaminic acid Dibenzyl N-[trans-2-(2'-acetylaminocyclohexyloxy)acetyl]-L-alanyl-D-glutamate (1180 mg, 1.98 mmoles) was dissolved in methanol (20 ml), nitrogen was blown through the solution, 160 mg of Pd/C (10%) were added and the mixture was hydrogenated at normal pressure for 1 hour. After the removal of the catalyst and evaporation of the solvent, there were obtained 820 mg (99%) of the title compound in the form of a white amorphous foam.

¹H-NMR (300 MHz, DMSO-d₆): δ=1.02-1.24 (m, 4H, 4H$_{ax}$), 1.19 (d, 3H, J=6.9 Hz, CH₃-Ala), 1.55-1.70 (m, 2H, 2 H$_{eq}$), 1.70-1.90 (m, 2H, CH₂-βGlu), 1.81 (1.83), (s, 3H, COCH₃), 1.95-2.15 (m, 2H, 2 H$_{eq}$), 2.24 (t, 2H, J=7.1 Hz, CH₂-γGlu), 3.10-3.20 (m, 1H, 2'-H), 3.50-3.70 (m, 1H, 1'-H), 3.93 (3.87)(AB-system, 2H, J=15.3 Hz, OCH₂), 4.18-4.30 (m, 1H, CH-Glu), 4.35-4.42 (m, 1H, CH-Ala), 7.54 (7.56)(d, 1H, NH), 7.94 (d, 1H, NH), 8.33 (8.35)(d, 1H, NH), 12.4 (s, 2H, 2 COOH) ppm.

Example 13

A. Benzyl N-[trans-2-(2'-acetylaminocyclohexyloxy)acetyl]-L-alanyl-D-isoglutaminate To a solution of benzyl L-alanyl-D-isoglutaminate hydrochloride (647 mg, 2 mmoles) and trans-2-(2'-acetylaminocyclohexyloxy) acetic acid (430 mg, 2 mmoles) in dry dimethylformamide (9 ml), there was added under stirring on ice bath diphenylphosphoryl azide (550 mg, 2 mmoles), followed by triethylamine (0.56 ml, 4 mmoles). The stirring was continued for another hour on ice bath and for 60 hours at room temperature. Ethyl acetate (40 ml) was added thereto and the mixture was extracted successively with 10% citric acid (3×5 ml), distilled water (3×5 ml), and saturated with NaCl solution (3×5 ml). All three aqueous phases were combined, saturated with NaCl and extracted with ethyl acetate (5×20 ml). All six ethyl acetate phases were combined and washed successively with saturated NaCHO₃ solution (3×15 ml), distilled water (3×15 ml) and saturated NaHCO₃ solution (3×15 ml). The mixture was dried with magnesium sulphate, the drying agent was filtered off and ethyl acetate was removed from the filtrate by distillation in vacuo. Thus, there were obtained 560 mg (37%) of the title compound, melting point 183°-185° C.

¹H-NMR (300 MHz, DMSO-d₆): δ=1.05-1.35 (m, 4H, 4H$_{ax}$), 1.23 (d, 3H, J=6.9 Hz, CH₃-Ala), 1.52-1.70 (m, 2H, 2H$_{eq}$), 1.70-1.85 (m, 2H, 2CH₂-βiGln), 1.80 (s, 3H, CH₃CO), 1.95-2.10 (m, 2H, 2 H$_{eq}$), 2.36 (t, 2H, J=7.8 Hz, CH₂-γiGln) 3.05-3.18 (m, 1H, 2'-H), 3.50-3.62 (m, 1H, 1'-H), 3,82 (AB-system, 2H, J=15.1 Hz, OCH₂), 4.14-4.25 (m, 1H, CH-iGln), 4.31 (m, 1H, J=7.0 Hz, CH-Ala), 5.08 (s, 2H, CH₂-benzyl), 7.13 (s, 1H, NH), 7.22-7.45 (m, 6H, 5H-arom.(benzyl), NH), 7.58 (d, 1H, J=7.08 Hz, NH), 7.88 (d, 1H, J=7.62 Hz, NH), 8.22 (d, 1H, J=8.1 Hz, NH) ppm.

B.
N-[Trans-2-(2'-acetylaminocyclohexyloxy)acetyl]-L-alanyl-D-isoglutamine The compound was prepared by hydrogenation of benzyl N-[trans-2-(2'-acetylaminocyclohexyloxy)acetyl]-L-alanyl-D-isoglutaminate in a manner as described in Example 12B.

Yield: 98% theor.
Melting point: 200°-203° C.

¹H-NMR (300 MHz, DMSO-d₆): δ=1.04-1.32 (m, 4H, 4H$_{ax}$), 1.24-1.25 (d, 3H, J=7.0 Hz, CH₃-Ala), 150-1.70 (m, 2H, 2H$_{eq}$), 1.67-1.82 (m, 2H, CH₂-βiGln), 1.81 (1.84)(s, 3H, COCH₃), 1.90-2.08 (m, 2H, 2H$_{eq}$), 2.21 (2.23)(t, 2H, J=7.6 Hz, CH₂-γiGln), 3.06-3.20 (m, 1H, 2'-H), 3.50-3.64 (m, 1H, 1'-H), 3.91 (3.92) (AB-system, 2H, J=15.1 Hz, OCH₂), 4.12-4.24 (m, 1H, CH-iGln), 4.31 (4.33)(m, 1H, J=7.0 Hz, CH-Ala), 7.11 (7,13)(s, 1H, NH), 7.35 (s, 1H, NH), 7.58 (7.61)(d, 1H, J=6.9 Hz, NH), 7.89 (7.92)(d, 1H, J=7.9 Hz, NH), 8.20 (827)(d, 1H, J=8.2 Hz, NH), 12.1 (s, 1H, COOH) ppm.

Example 14

A. Benzyl N-[trans-2-(2'-acetylaminocyclohexyloxy)propionyl]-L-alanyl-D-isoglutaminate The compound was prepared from trans-2-(2'-acetylaminocyclohexyloxy) propionic acid according to the process described in Example 13A.

Yield: 47% theor.
Melting point: decomposition above 140° C.
Analysis for C₂₆H₃₈N₄O₇:
calculated: 60.21% C, 7.39% H, 10.80% N.
found: 60.40% C, 7.58% H, 1061% N.

¹H-NMR (300 MHz, DMSO-d₆): δ=1.06-1.42 (m, 4H, 4H$_{ax}$), 1.16 (d, 3H, J=6.8 Hz, CH₃—), 1.19 (1.21)(d, 3H, J=6.4 Hz, CH₃-Ala), 1.43-1.88 (m, 4H, 2H$_{eq}$, CH₂-βiGln), 1.,79 (1.,80)(s, 3H, COCH₃), 1.88-2.12 (m, 2H, 2H$_{eq}$), 2.34 (2.35)(t, 2H, J=7.6 Hz, CH₂-γiGln), 3.02-3.21 (m, 1H, 2'-H), 3.52-3.67 (m, 1H, 1'-H), 3.87-3.99 (m, 1H, CH), 4.09-4.34 (m, 1H, CH-iGln), 4.24-4.35 (m, 1H, CH-Ala), 5.07 (s, 2H, CH₂-benzyl), 7.13 (s, 1H, NH), 7.24-7.50 (m, 6H, 5H-arom., NH), 7.60 (7.66)(d, 1H, J=7.1 Hz, NH), 7.74 (d, 1H, J=8.3 Hz, NH), 8.13 (8.18)(d, 1H, J=8.3 Hz, NH) ppm.

B.
N-[Trans-2-(2'-acetylaminocyclohexyloxy)propionyl]-L-alanyl-D-isoglutamine The compound was prepared from benzyl N-[trans-2-(2'-acetylaminocyclohexyloxy)propionyl]-L-alanyl-D-isoglutaminate in a manner as described in Example 12B.

Yield: 67% theor.
Melting point: 109° C.

¹H-NMR (300 MHz, DMSO-d₆): δ=1.08-1.35 (m, 4H, 4H$_{ax}$), 1.15 (d, 3H, J=6.6 Hz, CH₃), 1.22 (1.24)(d, 3H, J=6.7 Hz, CH₃-Ala), 1.43-1.80 (m, 4H, 2H$_{eq}$, CH₂-βiGln), 1.80 (1.81)(s, 3H, COCH₃), 1.88-2.09 (m, 2H, 2H$_{eq}$), 2.21 (t, 2H, J=7.4 Hz, CH₂-γiGln), 3.00-3.22 (m, 1H, 2'-H), 3.52-3.70 (m, 1H, 1'-H), 3.88-4.01 (m, 1H,

CH), 4.09–4.24 (m, 1H, CH-iGln), 4.24–4.38 (m, 1H, CH-Ala), 7.13 (s, 1H, NH), 7.24 (s, 1H, NH), 7.62 (7.65)(d, 1H, J=7.1 Hz, NH), 7.77 (d, 1H, J=8.5 Hz, NH), 8.14 (8.19)(d, 1H, J=7.9 Hz, NH) 12.3 (s, 1H, COOH) ppm.

Example 15

A. Benzyl N-[trans-2-(2'-p-toluenesulphonamidocyclohexyloxy)acetyl]-L-alanyl-D-isoglutaminate The compound was prepared from trans-2-(2'-p-toluenesulphonamidocyclohexyloxy) acetic acid according to the process as described in Example 13A. Thus, there was obtained a white amorphous solid foam. Yield: 97% theor.

$^1$H-NMR (300 MHz, CDCl$_3$): δ=1.00–1.35 (m, 4H, 4H$_{ax}$), 1.45 (1.48)(d, 3H, J=7.2 Hz, CH$_3$-Ala), 1.50–1.70 (m, 2H, 2H$_{eq}$), 1.95–2.60 (m, 6H, 2H$_{eq}$, 2CH$_2$iGln), 2.38 (2.39)(s, 3H, CH$_3$), 2.90–3.15 (m, 2H, 1'-H), 4.17 (AB-system, 2H, J=11.0 Hz, OCH$_2$), 4.36 (4.58)(m, 1H, J=7 Hz, CH-Ala), 4.42–4.52 (m, 1H, CH-iGln), 5.09 (5.10)(s, 2H, CH$_2$-benzyl), 6.10 (6.15)(s, 1H, NH), 6.31 (7.82)(d, 1H, J=6.5 Hz, NH), 6.75 (8.03)(d, 1H, J=7.7 Hz, NH), 7.08 (7.13)(s, 1H, NH), 7.25 (dd, 2H, J=8.0 Hz, 2H-arom.), 7.32 (7.33)(s, 5H, 5H-arom.(benzyl), 7.51 (7.60)(d, 1H, J=7.9 Hz, NH), 7.74 (dd, 2H, J=8.0 Hz, 2H-arom.) ppm.

B. N-[Trans-2-(2'-p-toluenesulphonamidocyclohexyloxy)acetyl]-L-alanyl-D-isoglutamine The compound was prepared from benzyl N-[trans-2-(2'-p-toluenesulphonamidocyclohexyloxy)acetyl]-L-alanyl-D-iso-glutaminate according to the process as described in Example 12B. Thus, there was obtained a white amorphous solid foam. Yield: 99% theor.

$^1$H-NMR (300 MHz, DMSO-d$_6$): δ=1.00–1.25 (m, 4H, 4H$_{ax}$), 1.27 (d, 3H, J=6.0 Hz, CH$_3$-Ala), 1.40–1.60 (m, 2H, 2H$_{eq}$), 1.60–2.10 (m, 4H, 2H$_{eq}$, CH2-βiGln), 2.18–2.28 (m, 2H, CH$_2$-γiGln), 2.37 (s, 3H, CH$_3$-tosyl), 2.80–3.00 (m, 1H, 2'-H), 3.00–3.15 (m, 1H, 1'-H), 3.84 (3.86)(AB-system, 2H, J=15.5 Hz, OCH$_2$), 4.15–4.28 (m, 1H, CH-iGln), 4.36 (m, 1H, CH-Ala), 7.10 (s, 1H, NH), 7.35 (dd, 2H, J=8.2 Hz, 2H-arom.), 7.70 (dd, 2H, J=8.0 Hz, 2H-arom.), 7.39 (s, 1H, NH), 7.80–7.92 (m, 2H, 2NH), 8.22 (8.26)(d, 1H, J=8.0 Hz, NH), 122 (s, 1H, COOH) ppm.

Example 16

A. Benzyl N-[trans-2-(2'-p-toluenesulphonamidocyclohexyloxy)-propionyl]-L-alanyl-D-isoglutaminate The compound was prepared from trans-2-(2'-p-toluenesulphonamidocyclohexyloxy) propionic acid in a manner as described in Example 13A. Thus, there was obtained a white solid amorphous foam. Yield: 70% theor.

$^1$H-NMR (300 MHz, DMSO-d$_6$): δ=0.95–1.25 (m, 4H, 4H$_{ax}$), 1.06 (1.09) (d, 3H, J=6.3 Hz, CH$_3$), 1.21 (d, 3H, J=6.9 Hz, CH$_3$-Ala), 1.40–1.60 (m, 2H, 2H$_{eq}$), 1.70–2.10 (m, 4H, 2H$_{eq}$, CH$_2$-βiGln), 2.25–2.45 (m, 2H, CH$_2$-γiGln), 2.35 (s, 3H, CH$_3$), 2.92–3.10 (m, 2H, 1'-H, 2'-H), 3.88–4.00 (m, 1H, CH), 4.15–4.35 (m, 2H, CH-Ala, CH-iGln), 5.08 (s, 2H, CH$_2$-benzyl), 7.15 (s, 1H, NH), 7.25–7.50 (m, 9H, 2H-arom. (tosyl), 5H-arom.(benzyl), 2NH), 7.55–7.62 (m, 2H, 2NH), 7.70 (dd, 2H, J=7.3 Hz, 2H-arom.), 8.19 (d, 1H, J=8.1 Hz, NH) ppm.

B. N-[Trans-2-(2'-p-toluenesulphonamidocyclohexyloxy)-propionyl]-L-alanyl-D-isoglutamine The compound was prepared from benzyl N-[trans-2-(2'-p-toluenesulphonamidocyclohexyloxy)propionyl]-L-alanyl-D-iso-glutaminate according to the process as described in Example 12B. Thus, there was obtained a white solid amorphous foam. Yield: 62% theor.

$^1$H-NMR (300 MHz, DMSO-d$_6$): δ=0.95–1.30 (m, 4H, 4H$_{ax}$), 1.08 (d, 3H, J=6.1 Hz, CH$_3$), 1.23 (d, 3H, J=6.6 Hz, CH$_3$-Ala), 1.40–1.60 (m, 2H, 2H$_{eq}$), 1.62–2.05 (m, 4H, 2H$_{eq}$, CH$_2$-βiGln), 2.21 (t, 2H, J=7.6 Hz, CH$_2$-γiGln), 2.36 (s, 3H, CH$_3$), 2.90–3.10 (m, 2H, 1'-H, 2'-H), 3.88–4.00 (m, 1H, CH), 4.15–4.35 (m, 2H, CH-Ala, CH-iGln), 7.13 (s, 1H, NH), 7.32–7.44 (m, 3H, 2H-arom., NH), 7.52–7.64 (m, 2H, 2NH), 7.70 (dd, 2H, J=8.0 Hz, 2H-arom.), 8.17 (d, 1H, J=8.0 Hz, NH), 12.1 (s, 1H, COOH) ppm.

Example 17

A. Benzyl N-[trans-2-(2'-(N'-phenylureido)cyclohexyloxy)acetyl]-L-alanyl-D-isoglutaminate The compound was prepared from trans-2-[2'-(N'-phenylureido)cyclohexyloxy] acetic acid according to the process as described in Example 13A.

Yield: 71% theor.

Melting point: 163°–165° C.

$^1$H-NMR (300 MHz, DMSO-d$_6$): δ=1.10–1.40 (m, 4H, 4H$_{ax}$), 1.15 (1.17)(d, 3H, J=6.8 Hz, CH$_3$-Ala), 1.50–1.75 (m, 2H, 2H$_{eq}$), 1.75–2.10 (m, 4H, 2H$_{eq}$, CH$_2$-βiGln), 2.36 (2.38)(t, 2H, J=7.4 Hz, CH$_2$-γiGln), 3.15–3.28 (m, 1H, 2'-H), 3.50–3.62 (m, 1H, 1'-H), 3.95 (3.94)(AB-system, 2H, J=15.4 Hz, OCH$_2$), 4.12–4.30 (m, 1H, CH-iGln), 4.28 (4.37)(m, 1H, J=7.0 Hz, CH-Ala), 5.08 (s, 2H, CH$_2$-benzyl), 6.23 (6.25) (d, 1H, J=7.5 Hz, NH), 6.86 (dd, 1H, H-arom.), 7.10–7.25 (m, 3H, 2H-arom., NH), 7.25–7.50 (m, 8H, 5H-arom.(benzyl), 2H-arom., NH), 7.59 1 (7.66)(d, 1H, J=6.9 Hz, NH), 8.22 (8.37)(d, 1H, J=8.0 Hz, NH), 8.36 (s, 1H, NH) ppm.

B. N-[Trans-2-(2'-(N'-phenylureido)cyclohexyloxy)acetyl]-L-alanyl-D-isoglutamine The compound was prepared from benzyl N-[trans-2-(2'-(N'-phenylureido)cyclohexyloxy)acetyl]-L-alanyl-D-isoglutaminate according to the process described in Example 12B.

Yield: 72% theor.

Melting point: 196°–198° C.

$^1$H-NMR (300 MHz, DMSO-d$_6$): δ=1.05–1.40 (m, 4H, 4H$_{ax}$), 1.16 (1.18)(d, 3H, J=6.8 Hz, CH$_3$-Ala), 1.50–2.08 (m, 6H, 4H$_{eq}$, CH$_2$-βiGln), 2.20 (2.23)(t, 2H, J=7.1 Hz, CH$_2$-γiGln), 3.15–3.28 (m, 1H, 2'-H), 3.50–3.65 (m, 1H, 1'-H), 3.94 (3.95) (AB-system, 2H, J=15.3 Hz, OCH$_2$), 4.10–4.25 (m, 1H, CH-iGln), 4.29 (4.40)(m, 1H, J=7.0 Hz, CH-Ala), 6.28 (6.29)(d, 1H, J=7.8 Hz, NH), 6.87 (dd, 1H, 1H-arom.), 7.05–7.50 (m, 6H, 4H-arom., CONH$_2$), 7.58 (7.66)(d, 1H, J=6.9 Hz, NH), 8.20 (8.35)(d, 1H, J=8.2 Hz, NH), 8.41 (s, 1H, NH), 12.1 (s, 1H, COOH) ppm.

Example 18

A. Benzyl N-[trans-2-(2'-t-butyloxycarbonylaminocyclohexyloxy)acetyl]-L-alanyl-D-isoglutaminate The compound was prepared from trans-2-(2'-t-butyloxycarbonylaminocyclohexyloxy) acetic acid according to the process as described in Example 13A. Thus, there was obtained a solid white amorphous foam. Yield: 86% theor.

$^1$H-NMR (300 MHz, DMSO-d$_6$): δ=1.00–1.50 (m, 4H, 4H$_{ax}$), 1.23 (1.24)(d, 3H, J=6.8 Hz, CH$_3$-Ala), 1.36 (s, 9H, C(CH$_3$)$_3$), 1.50–1.68 (m, 2H, 2H$_{eq}$), 1.70–1.90 (m, 2H, CH$_2$-βiGln), 1.90–2.10 (m, 2H, 2H$_{eq}$), 2.36 (t, 2H, J=7.6 Hz, CH$_2$-γiGln), 3.00–3.32 (m, 2H, 1'-H, 2'-H), 3.93 (AB-system, 2H, J=15.6 Hz, OCH$_2$), 4.15–4.28 (m, 1H, CH-iGln), 4.28–4.40 (m, 1H, CH-Ala), 5.08 (s, 2H, CH$_2$-benzyl), 6.85 (6.93)(d, 1H, J=7.5 Hz, NH), 7.13 (s, 1H, NH), 7.22–7.50 (m, 6H, 5H arom., NH), 7.55 (7.61) (d, 1H, J=7.0 Hz, NH), 8.23 (8.27)(d, 1H, J=8.2 Hz, NH) ppm.

B. N-[Trans-2-(2'-t-butyloxycarbonylaminocyclohexyloxy)acetyl]-L-alanyl-isoglutamine The compound was prepared from benzyl N-[trans-2-(2'-t-butyloxycarbonylaminocyclohexyloxy)acetyl]-L-alanyl-D-isoglutaminate according to the process as described in Example 12B. Thus, there was obtained a solid white amorphous foam. Yield: 98% theor.

$^1$H-NMR (300 MHz, DMSO-d$_6$): δ=1.00–1.42 (m, 4H, 4H$_{ax}$), 1.23 (d, 3H, J=6.9 Hz, CH$_3$-Ala), 1.36 (s, 9H, C(CH$_3$)$_3$), 1.48–1.64 (m, 2H, 2H$_{eq}$), 1.64–1.87 (m, 2H, CH$_2$-βiGln), 1.87–2.08 (m, 2H, 2H$_{eq}$), 2,19 (t, 2H, J=7.7 Hz, CH$_2$-γiGln), 3.08–3.35 (m, 2H, 1'-H, 2'-H), 3.92 (AB-system, 2H, J=15.5 Hz, OCH$_2$), 4.08–4.25 (m, 1H, CH-iGln), 4.25–4.43 (m, 1H, CH-Ala), 6.84 (6.92)(d, 1H, J=7.7 Hz, NH), 7.09 (s, 1H, NH), 7.43 (s, 1H, NH), 7.53 (7.58)(d, 1H, J=8.4 Hz, NH), 8.19 (8.21)(d, 1H, J=8.4 Hz, NH), 12.08 (s, 1H, COOH) ppm.

PREPARATION OF COMPOUNDS OF FORMULA Ia AND OF COMPOUNDS OF FORMULA Ib

Example 19

(1'S,2'S)-trans-N-(2'-hydroxycyclohexyl)-2-chloroacetamide

To a solution of (1S,2S)-trans-2-aminocyclohexanol (1.15 g, 10 mmoles) in a mixture of acetone (20 ml) and water (7 ml) there was added sodium acetate (1.64 g, 20 mmoles), followed by dropwise addition of chloroacetyl chloride (1.13 g, 10 mmoles) within 5 minutes at the temperature of +5° C. and under stirring. After 4 hours of stirring at room temperature, the mixture was evaporated to dryness and chloroform (50 ml) was added thereto. The organic phase was washed with water (20 ml) and then with saturated NaCl solution (20 ml), dried with magnesiumsulphate, filtered, and chloroform was evaporated. Thus, there were obtained 1.54 g (81%) of the title compound, which was recrystallized from ethyl acetate.

Melting point: 137°–139° C.

[α]$_D^{20}$=+46.7 (c=0.1; methanol).

IR (KBr): 3308, 2944, 2856, 1645, 1548, 1456, 1409, 1264, 1060, 1046, 974, 772 cm$^{-1}$.

$^1$H-NMR (300 MHz, DMSO-d$_6$): δ=1.00–1.30 (m, 4H, 4H$_{ax}$), 1.42–1.70 (m, 2H, 2H$_{eq}$), 1.70–1.90 (m, 2H, 2H$_{eq}$), 3.18–3.30 (m, 1H, 1'-H), 3.30–3.42 (m, 1H, 2'-H), 4.01 (s, 2H, CH$_2$Cl), 4.58 (d, 1H, J=5.04 Hz, OH), 7.96 (d, 1H, J=7.86 Hz, NH) ppm.

$^{13}$C-NMR (75.44 MHz, DMSO-d$_6$): δ=23.2, 23.5, 30.2, 33.5, 42.4, 54.2, 70.3, 164.8 ppm.

Example 20

(1'R,2'R)-trans-N-(2'-hydroxycyclohexyl)-2-chloroacetamide

The compound was prepared from (1R,2R)-trans-2-aminocyclohexanol (1.15 g, 10 mmoles) in a manner analogous to the one described in Example 19. Thus, there were obtained 1.34 g (70%) of the title compound.

Melting point: 138°–140° C.

[α]$_D^{20}$=−39.6 (c=0.1; methanol).

IR (KBr): The spectrum is identical with the IR spectrum of Example 19.

$^1$H-NMR (300 MHz, DMSO-d$_6$): The spectrum was identical with the $^1$H-NMR spectrum of Example 19.

$^{13}$C-NMR (75.44 MHz, DMSO-d$_6$): The spectrum was identical with the $^{13}$C-NMR spectrum of Example 19.

Example 21

(4aR,8aR)-trans-octahydro-2H-1,4-benzoxazine-3-one (1'R,2'R)-trans-N-(2'-hydroxycyclohexyl)-2-chloroacetamide (1.783 g, 9.3 mmoles) was suspended in anhydrous tetrahydrofurane (25 ml) and at the temperature of +2° C. NaH (0.268 g, 11.16 mmoles) was added thereto under stirring. The stirring was continued for another hour on ice bath and then for 14 hours at room temperature. After the addition of water (6 ml) the reaction mixture was stirred for 20 minutes, followed by evaporation to dryness and addition of chloroform (50 ml). After washing with water (20 ml) and saturated NaCl solution (20 ml), the organic phase was dried with magnesium sulphate, filtered and chloroform was filtered off. Thus, there were obtained 1.36 g (94%) of the title compound, which was recrystallized from ethyl acetate.

Melting point: 165°–167° C.

[α]$_D^{20}$=−46.1 (c=0.1; methanol)

IR (KBr): 3182, 3079, 2938, 2863, 1700, 1646, 1415, 1379, 1360, 1306, 1109, 793, 490 cm$^{-1}$.

$^1$H-NMR (300 MHz, CDCl$_3$): δ=1.18–1.45 (m, 4H, 4H$_{ax}$), 1.65–2.05 (m, 4H, 4H$_{eq}$), 3.10–3.26 (m, 2H, 4a-H, 8a-H), 4.24 (AB-system, 2H, J=16.85 Hz, OCH$_2$), 7.80 (br. s, 1H, NH) ppm.

$^{13}$C-NMR (75.44 MHz, CDCl$_3$): δ=23.3, 24.1, 29.7, 30.6, 55.7, 67.8, 77.8, 169.8 ppm.

Example 22

(4aS,8aS)-trans-octahydro-2H-1,4-benzoxazine-3-one

The compound was prepared from (1'S,2'S)-trans-N-(2'-hydroxycyclohexyl)-2-chloroacetamide (1.92 g, 10 mmoles) in a manner analogous to the one described in Example 21. Thus, there were obtained 1.44 g (91%) of the title compound.

Melting point: 165°–167° C.

[α]$_D^0$=+45.2 (c=0.1; methanol).

IR (KBr): The spectrum was identical with the IR spectrum of Example 21.

$^1$H-NMR (300 MHz, CDCl$_3$): The spectrum was identical with the $^1$H-NMR spectrum of Example 21.

$^{13}$C-NMR (75.44 MHz, CDCl$_3$): The spectrum was identical with the $^{13}$C-NMR spectrum of Example 21.

Example 23

(1R,2R)-trans-2-carboxymethoxy-cyclohexylammonium chloride

A solution of (4aR,8aR)-trans-octahydro-2H-1,4-benzoxazine-3-one (1.20 g, 7.73 mmoles) in a mixture of 37% hydrochlorid acid (21 ml) and water (21 ml) was heated for 4 hours at reflux temperature, the reaction mixture was evaporated to dryness in vacuo and the solid residue was recrystallized from a mixture of ethanol/ether. Thus, there were obtained 1.47 g (91%) of the title compound in the form of white crystals.

Melting point: 217°–220° C.

$[\alpha]_D = -9.45$ (c=0.1; methanol).

IR (KBr): 3650–2400, 1735, 1600, 1582, 1484, 1412, 1219, 1129, 1036, 1008, 823, 685 cm$^{-1}$.

$^1$H-NMR (300 MHz, DMSO-d$_6$): $\delta$=1.05–1.32 (m, 3H, 3H$_{ax}$), 1.35–1.55 (m, 1H, 1H$_{ax}$), 1.58–1.75 (m, 2H, 2H$_{eq}$), 1.95–2.05 (m, 1H, 1H$_{eq}$), 2.05–2.20 (m, 1H, 1H$_{eq}$), 2.80–2.95 (m, 1H, 1-H), 3.30–3.42 (m, 1H, 2-H), 4.15 (s, 2H, OCH$_2$), 8.25 (br.s, 3H, NH$_3$+), 12.85 (br.s, 1H, COOH) ppm.

$^{13}$C-NMR (75.44 MHz, DMSO-d$_6$): $\delta$=23.2, 23.3, 28.6, 29.5, 53.7, 65.6, 79.2, 172.6 ppm.

Example 24

(1S,2S)-trans-2-carboxymethoxy-cyclohexylammonium chloride

The compound was prepared from (4aS,8aS)-trans-octahydro-2H-1,4-benzoxazine-3-one (0.83 g, 5.35 mmoles) in a manner analogous to the one described in Example 23. Thus, there were obtained 864 mg (77%) of the title compound.

Melting point: 218°–220° C.

$[\alpha]_D^{20} = +92.4$ (c=0.1; methanol).

IR (KBr): The spectrum was identical with the IR spectrum of Example 23.

$^1$H-NMR (300 MHz, DMSO-d$_6$): The spectrum was identical with the $^1$H-NMR spectrum of Example 23.

$^{13}$C-NMR (75.44 MHz, DMSO-d$_6$): The spectrum was identical with the $^{13}$C-NMR spectrum of Example 23.

Example 25

(1'R,2'R)-trans-2-(2'-acetylaminocyclohexyloxy) acetic acid

To a solution of (1R,2R)-trans-2-carboxymethoxy-cyclohexylammonium chloride (1.34 g, 6.39 mmoles) in 2N aqueous NaOH solution (6.39 ml) cooled to 0° to +5° C., there were added under stirring first 1N NaOH (1.28 ml), followed by acetic anhydride (0.130 g, 1.28 mmoles). When the reaction of anhydride was completed and a homogeneous solution was obtained, the same amount of 1N NaOH and acetic anhydride as above was added four times. After the addition of the last portion the reaction mixture was stirred for 30 minutes, the solution was acidified to pH 2 and extracted with ethyl acetate. The organic phase was dried with MgSO$_4$, filtered and the filtrate was evaporated in vacuo. The residue was recrystallized from a mixture of chloroform/ethyl acetate/n-hexane. Thus, there were obtained 1.14 g (83%) of the title compound in the form of white amorphous chrystals.

Melting point: 130°–132° C.

$[\alpha]_D^{20} = -44.2$ (c=0.1; methanol).

IR (KBr): 3331, 2940, 2867, 1725, 1613, 1555, 1436, 1372, 1212, 1125, 894, 682, 660 cm$^{-1}$.

$^1$H-NMR (300 MHz, CDCl$_3$): $\delta$=0.95–1.10 (m, 1H, 1H$_{ax}$), 1.10–1.40 (m, 3H, 3H$_{ax}$), 1.60–1.70 (m, 1H, 1H$_{eq}$), 1.70–1.85 (m, 1H, 1H$_{eq}$), 2.00–2.20 (m, 1H, 1H$_{eq}$), 2.09 (s, 3H, CH$_3$), 2.45–2.60 (m, 1H, 1H$_{eq}$), 3.10–3.25 (m, 1H, 2'-H), 3.40–3.55 (m, 1H, 1'-H), 4.14 (AB-system, 2H, J=17.63 Hz, OCH$_2$), 8.45 (d, 1H, J=3.96 Hz, NH), 12.20 (br.s, 1H, COOH) ppm.

$^{13}$C-NMR (75.44 MHz, CDCl$_3$): $\delta$=22.3, 23.4, 23.8, 29.5, 30.4, 54.4, 64.4, 79.9, 172.3, 174.2 ppm.

Example 26

(1'S,2'S)-trans-2-(2'-acetylaminocyclohexyloxy) acetic acid

The compound was prepared from (1S,2S)-trans-2-carboxymethoxy-cyclohexylammonium chloride (0.67 g, 3.20 mmoles) in a manner analogous to the one described in Example 25. Thus, there were obtained 0.50 g (72%) of the title compound.

Melting point: 130°–132° C.

$[\alpha]_D^{20} = +43.5$ (c=0.1; methanol).

IR (KBr): The spectrum was identical with the IR spectrum of Example 25.

$^1$H-NMR (300 MHz, CDCl$_3$): The spectrum was identical with the $^1$H-NMR spectrum of Example 25.

$^{13}$C-NMR (75.44 MHz, CDCl$_3$): The spectrum was identical with the $^{13}$C-NMR spectrum of Example 25.

Example 27

(1'R,2'R)-dibenzyl-N-[trans-2-(2'-acetylaminocyclohexyloxy)acetyl-L-alanyl-D-glutamate To a solution of dibenzyl-L-alanyl-D-glutamate hydrochloride (869 mg, 2 mmoles) and (1'R,2'R)-trans-2-(2'-acetylaminocyclohexyloxy) acetic acid (430 mg, 2 mmoles) in dry N,N-dimethylformamide (10 ml) there was added, at +2° C. under stirring, diphenylphosphorylazide (550 mg, 2 mmoles), followed by triethylamine (0.56 ml, 4 mmoles). The stirring was continued for 1 hour at +2° C. and for 60 hours at room temperature. After the addition of ethyl acetate (40 ml), the reaction mixture was extracted successively with 10% citric acid (3×5 ml), distilled water (3×5 ml) and saturated NaCl solution (3×5 ml), saturated NaHCO$_3$ solution (3×5 ml), distilled water (3×5 ml), and saturated NaCl solution (3×5 ml). The organic phase was dried with magnesium sulphate and filtered and ethyl acetate was distilled off, yielding 1.19 g (100%) of the title compound in the form of a pale yellow viscous oil, which was purified by column chromatography (silica gel; chloroform/methanol=9/1).

$[\alpha]_D^{20} = -10.0$ (c=0.1; methanol).

IR (KBr); 3287, 3066, 2934, 2858, 1744, 1649, 1548, 1446, 1374, 1271, 1169, 966, 753, 696, 578 cm$^{-1}$.

$^1$H-NMR (300 MHz, DMSO-d$_6$): $\delta$=1.00–1.30 (m, 4H, 4H$_{ax}$), 1.23 (d, 3H, J=7.02 Hz, CH$_3$-Ala), 1.50–1.70 (m, 2H, 2H$_{eq}$), 1.80 (s, 3H, COCH$_3$), 1.80–2.12 (m, 4H, 2H$_{eq}$, CH$_2$-$\beta$Glu), 2.46 (t, 2H, J=7.60 Hz, CH$_2$-$\gamma$Glu), 3.06–3.18 (m, 1H, 2'-H), 3.50–3.62 (m, 1H, 1'-H), 3.91 (AB-system, 2H, J=15.14 Hz, OCH$_2$), 4.30–4.42 (m, 2H, CH-Glu, CH-Ala), 5.08 (s, 2H, CH$_2$-benzyl), 5.11 (s, 2H, CH$_2$-benzyl), 7.30–7.40 (m, 10H, 10H-arom.), 7.56 (d, 1H, J=7.78 Hz, NH), 7.89 (d, 1H, J=7.63 Hz, NH), 8.53 (d, 1H, J=7.78 Hz, NH) ppm.

$^{13}$C-NMR (75.44 MHz, DMSO-d$_6$): $\delta$=18.9, 22.8, 23.4, 23.7, 25.9, 29.7, 29.9, 31.0, 47.3, 51.2, 51.8, 65.5, 66.0, 67,3, 80.5, 127.7, 127.8, 127.9, 128.0, 128.4, 135.8, 136.0, 168.9, 169.2, 171.2, 171.9, 172.3 ppm.

Example 28

(1'S,2'S)-dibenzyl-N-[trans-2-(2'-acetylaminocyclohexyloxy)acetyl]-L-alanyl-D-glutamate The compound was prepared from dibenzyl-L-alanyl-D-glutamate hydrochloride (869 mg, 2 mmoles) and (1'S,2'S)-trans-2-(2'-acetylaminocyclohexyloxy) acetic acid (430 mg, 2 mmoles) in a manner analogous to the one described in Example 27. Thus, there were obtained 1.025 g (86%) of the title compound in the form of a pale yellow viscous oil.

$[\alpha]_D^{20} = +19.6$ (c=0.1; methanol).

IR (KBr): 3391, 3296, 3066, 2935, 2859, 1740, 1654, 1542, 1453, 1375, 1261, 1166, 1113, 967, 739, 698, 579 cm$^{-1}$.

$^1$H-NMR (300 MHz, DMSO-d$_6$): $\delta$=1.00–1.30 (m, 4H, 4H$_{ax}$), 1.23 (d, 3H, J=7.02 Hz, CH$_3$-Ala), 1.50–1.70 (m, 2H, 2H$_{eq}$), 1.80 (s, 3H, COCH$_3$), 1.80–2.12 (m, 4H, 2H$_{eq}$, CH$_2$-βGlu), 2.43 (t, 2H, J=7.63 Hz, CH$_2$-γGlu), 3.06–3.18 (m, 1H, 2'-H), 3.50–3.62 (m, 1H, 1'-H), 3.93 (AB-system, 2H, J=15.29 Hz, OCH$_2$), 4.30–4.42 (m, 2H, CH-Glu, CH-Ala), 5.08 (s, 2H, CH$_2$-benzyl), 5.12 (s, 2H, CH$_2$-benzyl), 7.30–7.40 (m, 10H, 10H-arom.), 7.53 (d, 1H, J=7.63 Hz, NH), 7.91 (d, 1H, J=7.75 Hz, NH), 8.49 (d, 1H, J=7,75 Hz, NH) ppm.

$^{13}$C-NMR (75.44 NHz, DMSO-d$_6$): $\delta$=18.8, 22.8, 23.4, 23.7, 25.9, 29.6, 29.9, 30.9, 47.4, 51.1, 51.8, 65.4, 65.9, 67.5, 80.7, 127.7, 127.8, 127.9, 128.3, 135.7, 135.9, 168.8, 169.2, 171.2, 171.8, 172.1 ppm.

Example 29

(1'R,2'R)-benzyl-N-[trans-2-(2'-acetylaminocyclohexyloxy)acetyl]-L-alanyl-D-isoglutaminate To a solution of benzyl-L-alanyl-D-isoglutaminate hydrochloride (687 mg, 2 mmoles) and (1'R,2'R)-trans-2-(2'-acetylaminocyclohexyloxy) acetic acid (430 mg, 2 mmoles) in dry dimethylformamide (10 ml) there was added, at +2° C. under stirring, diphenylphosphorylazide (550 mg, 2 mmoles), followed after 5 minutes by triethylamine (0.56 ml, 4 mmoles). The stirring was continued for 1 hour at +2° C. and for 60 hours at room temperature. After the addition of ethyl acetate (40 ml), the reaction mixture was extracted successively with 10% citric acid (3×5 ml), distilled water (3×5 ml) and saturated NaCl solution (3×5 ml). All three aqueous phases were combined, saturated with NaCl and extracted with ethyl acetate (5×20 ml). All six ethyl acetate phases were combined and washed successively with saturated NaHCO$_3$ solution (3×15 ml), distilled water (3×15 ml) and saturated NaHCO$_3$ solution (3×15 ml). The mixture was dried with magnesium sulphate, filtered and ethyl acetate was distilled off in vacuo. Thus, there were obtained 590 mg (58%) of the title compound, which was recrystallized from a mixture of ethyl acetate/methanol.

Melting point: 173°–175° C.

$[\alpha]_D^{20} = -20.0$ (c=0.1; methanol).

IR (KBr): 3290, 3089, 2938, 2859, 1735, 1648, 1553, 1450, 1376, 1318, 1238, 1171, 1127, 1101, 965, 745, 695, 608 cm$^{-1}$.

$^1$H-NMR (300 MHz, DMSO-d$_6$): $\delta$=1.05–1.35 (m, 4H, 4H$_{ax}$), 1.23 (d, 1H, J=6.89 Hz, CH$_3$-Ala), 1.55–1.70 (m, 2H, 2H$_{eq}$), 1.70–1.85 (m, 2H, CH$_2$-βiGln), 1.80 (s, 3H, CH$_3$CO), 1.95–2.10 (m, 2H, 2H$_{eq}$), 2.36 (t, 2H, J=7,81 Hz, CH$_2$-γiGln), 3.05–3.18 (m, 1H, 2'-H), 3.50–3.60 (m, 1H, 1'-H), 3.92 (AB-system, 2H, J=15.14 Hz, OCH$_2$), 4.15–4.25 (m, 1H, CH-iGln), 4.32 (m, 1H, CH-Ala), 5.08 (s, 2H, CH$_2$-benzyl), 7.13 (s, 1H, NH), 7.22–7.45 (m, 6H, 5H-arom., NH), 7.58 (d, 1H, J=7,08 Hz, NH), 7.88 (d, 1H, J=7.62 Hz, NH), 8.22 (d, 1H, J=8.06 Hz, NH) ppm.

Example 30

(1'S,2'S)-benzyl-N-[trans-2-(2'-acetylaminocyclohexyloxy)acetyl]-L-alanyl-D-isoglutaminate The compound was prepared from benzyl-L-alanyl-D-isoglutaminate hydrochloride (687 mg, 2mmoles) and (1',2'S)-trans-2-(2'-acetylaminocyclohexyloxy) acetic acid (430 mg, 2mmoles) in a manner analogous to the one described in Example 29. Thus, there were obtained 540 mg (43%) of the title compound.

Melting point: 199°–202° C.

$[\alpha]_D^{20} = +13.9$ (c=0.1; methanol).

IR (KBr): 3410, 3353, 3277, 3180, 3075, 2946, 2859, 1729, 1655, 1555, 1452, 1369, 1271, 1174, 1101, 964, 918, 854, 750, 694, 610 cm$^{-1}$.

$^1$H-NMR (300 MHz, DMSO-d$_6$): $\delta$=1.05–1.35 (m, 4H, 4H$_{ax}$), 1.21 (d, 1H, J=6.84 Hz, CH$_3$-Ala), 1.55–1.65 (m, 2H, 2H$_{eq}$), 1.70–1.85 (m, 2H, CH$_2$-βiGln), 1.79 (s, 3H, CH$_3$CO), 1.95–2.10 (m, 2H, 2H$_{eq}$), 2.35 (t, 2H, J=7,62 Hz, CH$_2$-γiGln), 3.05–3.18 (m, 1H, 2'-H), 3.50–3.60 (m, 1H, 1'-H), 3.90 (AB-system, 2H, J=15.38 Hz, OCH$_2$), 4.15–4.25 (m, 1H, CH-iGln), 4.30 (m, 1H, CH-Ala), 5.07 (s, 2H, CH$_2$-benzyl), 7.12 (s, 1H, NH), 7.22–7.45 (m, 6H, 5H-arom., NH), 7.57 (d, 1H, J=7.08 Hz, NH), 7.87 (d, 1H, J=7.82 Hz, NH), 8.20 (d, 1H, J=8.30 Hz, NH) ppm.

Example 31

(1'R,2'R)-N-[trans-2-(2'-acetylaminocyclohexyloxy)acetyl]-L-alanyl-D-glutaminic acid (1'R,2'R)-dibenzyl-N-[trans-2-(2'-acetylaminocyclohexyloxy)acetyl]-L-alanyl-D-glutamate (596 mg, 1 mmole) was dissolved in methanol (20 ml), nitrogen was blown through, 90 mg of Pd/C (10%) were added and the solution was hydrogenated for 1 hour at normal pressure. The catalyst was filtered off and methanol was evaporated in vacuo. Thus, there were obtained 411 mg (99%) of the title compound in the form of a solid white amorphous foam.

$[\alpha]_D^{20} = -27.59$ (c=0.1; methanol).

IR (KBr): 3340, 3096, 2939, 2900–2500 broad, 1734, 1654, 1542, 1449, 1378, 1213, 1116, 969, 856, 668, 586 cm$^{-1}$.

$^1$H-NMR (300 MHz, DMSO-d$_6$): $\delta$=b 1.05–1.25 (m, 4H, 4H$_{ax}$), 1.24 (d, 3H, J=7.02 Hz, CH$_3$-Ala), 1.55–1.70 (m, 2H, 2H$_{eq}$), 1.70–1.90 (m, 2H, CH$_2$-βGlu), 1.82 (s, 3H, COCH$_3$), 1.95–2.10 (m, 2H, 2H$_{eq}$), 2.26 (t, 2H, J=7.3 Hz, CH$_2$-γGlu), 3.10–3.20 (m, 1H, 2'-H), 3.50–3.65 (m, 1H, 1'-H), 3.91 (AB-system, 2H, J=15.26 Hz, OCH$_2$), 4.18–4.30 (m, 1H, CH-Glu), 4.40 (m, 1H, J=7.0 Hz, CH-Ala), 7.54 d, 1H, J=7.78 Hz, NH), 7.91 (d, 1H, J=7.75 Hz, NH), 8.35 (d, 1H, J=7.93 Hz, NH), 12.4 (br.s, 2H, 2COOH) ppm.

$^{13}$C-NMR (75.44 MHz, DMSO-d$_6$): $\delta$=19.1, 22.9, 23.5, 23.8, 26.4, 29.9, 29.9, 31.1, 47.3, 51.1, 51.8, 67.4, 80.5, 169.1, 169.2, 172.1, 173.0, 173.6 ppm.

Analysis for C$_{18}$H$_{29}$N$_3$O$_8$×0.5H$_2$O:
calculated: 50.93% C, 7.12% H, 9.90% N.
found: 50.93% C, 7.47% H, 9.82% N.

Example 32

(1'S,2'S)-N-[trans-2-(2'-acetylaminocyclohexyloxy)acetyl]-L-alanyl-D-glutaminic acid The compound was prepared by hydrogenating (1'S,2'S)-dibenzyl-N-[trans-2-(2'-acetylaminocyclohexyloxy)acetyl]-L-alanyl-D-glutamate (596 mg, 1 mmole) in a manner as described in Example 31. Thus, there were obtained 407 mg (98%) of the title compound in the form of a solid white amorphous foam.

$[\alpha]_D^{20} = +14.3$ (c=0.1; methanol).

IR (KBr): 3338, 3083, 2938, 2900–2300 broad, 1734, 1654, 1543, 1449, 1377, 1211, 1115, 969, 857, 668, 590 cm$^{-1}$.

$^1$H-NMR (300 MHz, DMSO-d$_6$): δ=1.05–1.25 (m, 4H, 4H$_{ax}$), 1.25 (d, 3H, J=6.94 Hz, CH$_3$-Ala), 1.55–1.70 (m, 2H, 2H$_{eq}$), 1.70–1.90 (m, 2H, CH$_2$-βGlu), 1.81 (s, 3H, COCH$_3$), 1.90–2.10 (m, 2H, 2H$_{eq}$), 2.26 (t, 2H, J=6.9 Hz, CH$_2$-γGlu), 3.10–3.20 (m, 1H, 2'-H), 3.50–3.60 (m, 1H, 1'-H), 3.93 (AB-system, 2H, J=15.26 Hz, OCH$_2$), 4.18–4.25 (m, 1H, CH-Glu), 4,38 (m, 1H, J=7.0 Hz, CH-Ala), 7.52 (d, 1H, J=7.78 Hz, NH), 7.91 (d, 1H, J=7.72 Hz, NH), 8.31 (d, 1H, J=8.09 Hz, NH), 12.0 (br.s, 2H, 2COOH) ppm.

$^{13}$C-NMR (75.44 MHz, DMSO-d$_6$): δ=19.1, 22.9, 23.4, 23.7, 26.4, 29.9, 30.1, 31.0, 47.5, 51.0, 51.9, 67.7, 80.7, 168.9, 169.2, 171.9, 173.0, 173.6 ppm.

Analysis for C$_{18}$H$_{29}$N$_3$O$_8$×0.5H$_2$O:
calculated: 50.93% C, 7.12% H, 9.90% N.
found: 51.38% C, 7.57% H, 9.72% N.

Example 33

(1'R,2'R)-N-[trans-2-(2'-acetylaminocyclohexyloxy)acetyl]-L-alanyl-D-isoglutamine The compound was prepared by hydrogenating (1'R,2'R)-benzyl-N-[trans-2-(2'-acetylaminocyclohexyloxy)acetyl]-L-alanyl-D-isoglutaminate (505 mg, 1 mmole) in a manner as described in Example 31. Thus, there were obtained 385 mg (93%) of the title compound.

Melting point: 216°–218° C.

$[\alpha]_D^{20} = -25.4$ (c=0.1; methanol).

IR (KBr): 3291, 3084, 2938, 2861, 1731, 1647, 1554, 1149, 1373, 1247, 1122, 1036, 971, 935, 845, 578 cm$^{-1}$.

$^1$H-NMR (300 MHz, DMSO-d$_6$): δ=1.04–1.34 (m, 4H, 4H$_{ax}$), 1.24 (d, 1H, J=7.02 Hz, CH$_3$-Ala), 1.50–1.70 (m, 2H, 2H$_{eq}$), 1.67–1.82 (m, 2H, CH$_2$-βiGln), 1.84 (s, 3H, CH$_3$CO), 1.90–2.08 (m, 2H, 2H$_{eq}$), 2.23 (t, 2H, J=7.57 Hz, CH$_2$-γiGln), 3.05–3.20 (m, 1H, 2'-H), 3.50–3.64 (m, 1H, 1'-H), 3.91 (AB-system, 2H, J=15.10 Hz, OCH$_2$), 4.12–4.24 (m, 1H, CH-iGln), 4.31 (m, 1H, J=7.0 Hz, CH-Ala), 7.13 (s, 1H, NH), 7.35 (s, 1H, NH), 7.58 (d, 1H, J=6.89 Hz, NH), 7.92 (d, 1H, J=7.81 Hz, NH), 8.27 (d, 1H, J=8.30 Hz, NH), 12,1 (br.s, 1H, COOH) ppm.

Example 34

(1'S,2'S)-N-[trans-2-(2'-acetylaminocyclohexyloxy)acetyl]-L-alanyl-D-isoglutamine The compound was prepared by hydrogenating (1'S,2'S)-benzyl-N-[trans-2-(2'-acetylaminocyclohexyloxy)acetyl]-L-alanyl-D-isoglutaminate (505 mg, 1 mmole) in a manner as described in Example 31. Thus, there were obtained 385 mg (93%) of the title compound in the form of a solid white amorphous foam.

$[\alpha]_D^{20} = +18.6$ (c=0.1; methanol).

IR (KBr): 3393, 3095, 2938, 2862, 1731, 1654, 1546, 1449, 1377, 1247, 1117, 1037, 973, 938, 861, 577 cm$^{-1}$.

$^1$H-NMR (300 MHz, DMSO-d$_6$): δ=1.04–1.30 (m, 4H, 4H$_{ax}$), 1.24 (d, 3H, J=7.02 Hz, CH$_3$-Ala), 1.54–1.68 (m, 2H, 2H$_{eq}$), 1.68–1.80 (m, 2H, CH$_2$-βiGln), 1.81 (s, 3H, CH$_3$CO), 1.90–2.06 (m, 2H, 2H$_{eq}$), 2.21 (t, 2H, J=7.55 Hz, CH$_2$-γiGln), 3.06–3.18 (m, 1H, 2'-H), 3.50–3.62 (m, 1H, 1'-H), 3.92 (AB-system, 2H, J=15.14 Hz, OCH$_2$), 4.12–4.24 (m, 1H, CH-iGln), 4.33 (m, 1H, J=7.03 Hz, CH-Ala), 7.13 (s, 1H, NH), 7.35 (s, 1H, NH), 7.58 (d, 1H, J=6.89 Hz, NH), 7.89 (d, 1H, J=7.81 Hz, NH), 8.20 (d, 1H, J=8.30 Hz, NH), 12.1 (br.s, 1H, COOH) ppm.

Example 35

Separation of a diastereoisomeric mixture of benzyl-N-[trans-2-(2'-acetylaminocyclohexyloxy)acetyl]-L-alanyl-D-isoglutaminate The diastereoisomeric mixture of benzyl-N-[trans-2-(2'-acetylaminocyclohexyloxy)acetyl]-L-alanyl-D-isoglutaminate (1 g) was separated on a column (silica gel, 0.063 to 0.2 mm; chloroform/methanol=9/1). Thus, there were obtained 470 mg of (1'R,2'R)-benzyl-N-[trans-2-(2'-acetylaminocyclohexyloxy)acetyl]-L-alanyl-D-isoglutaminate having the melting point, specific rotation as well as IR, $^1$H and $^{13}$C-NMR spectra identical with those of the product of Example 29 and 360 mg of (1'S,2'S)-benzyl-N-[trans-2-(2'-acetylaminocyclohexyloxy)acetyl]-L-alanyl-D-isoglutaminate having the melting point, specific rotation as well as IR, $^1$H and $^{13}$C-NMR spectra identical with those of the product of Example 30.

We claim:

1. Trans-2-acylaminocyclohexyloxyacyldipeptides of formula I

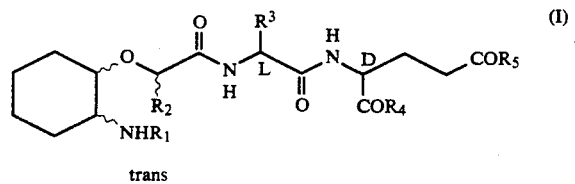

trans wherein

R$_1$ represents —CO—R$_6$, —SO$_2$—R$_7$ or

wherein

R$_6$ is a straight or branched chain C$_1$–C$_{18}$ alkyl group or a C$_1$–C$_{18}$ alkoxy group, R$_7$ is a straight or branched chain C$_1$–C$_{18}$ alkyl group, a phenyl group or a phenyl group substituted by a straight or branched chain lower C$_1$–C$_6$ alkyl group or halogen, Y is =O, =S or =NH;

R$_2$ and R$_3$, which are identical, represent —H or a straight or branched chain C$_1$–C$_{12}$ alkyl group;

R$_4$ represents —OR$_8$ or —NHR$_9$, wherein

R$_8$ is —H, a straight or branched chain C$_1$–C$_8$ alkyl group or benzyl group, R$_9$ is —H, a straight or branched chain C$_1$–C$_{18}$ alkyl group or benzyl group;

R$_5$ represents —OR$_9$ or —NHR$_9$, and the pharmaceutically acceptable alkali salts thereof.

2. Compound selected from the group consisting of (1R,2R)-Trans-2-acylaminocyclohexyloxyacetyldipeptides of the formula Ia

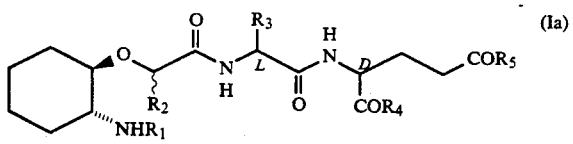

wherein
- $R_1$ represents —CO—$R_6$, wherein
  - $R_6$ is a straight or branched chain $C_1$-$C_{18}$ alkyl group;
- $R_2$ represents hydrogen;
- $R_3$ represents —H or a straight or branched chain $C_1$-$C_{12}$ alkyl group;
- $R_4$ represents —$OR_8$ or —$NHR_9$, wherein
  - $R_8$ is —H, a straight or branched chain $C_1$-$C_8$ alkyl group or benzyl group,
  - $R_9$ is —H, a straight or branched chain $C_1$-$C_{18}$ alkyl group or benzyl group,
- $R_5$ represents —$OR_9$ or —$NHR_9$;

and the pharmaceutically acceptable alkali salts thereof; (1S,2S)-acylaminocyclohexyloxyacetyldipeptides of the formula Ib

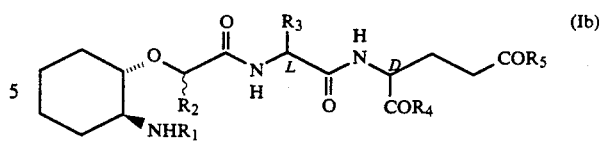

wherein $R_1$, $R_2$, $R_3$, $R_4$ and $R_5$ have the same meaning as in formula Ia, and the pharmaceutically acceptable alkali salts thereof.

3. Pharmaceutical preparations comprising a therapeutically effective amount of trans-2-acylaminocyclohexyloxyacyldipeptide of claim 1 as the active ingredient together with common pharmaceutically acceptable carriers and adjuvants.

4. Pharmaceutical preparations comprising a therapeutically effective amount of (1R,2R)-trans-2-acylaminocyclohexyloxyacetyldipeptide of claim 2 as the active ingredient together with common pharmaceutically acceptable carriers and adjuvants.

5. Pharmaceutical preparations comprising a therapeutically effective amount of (1S,2S)-trans-2-acylaminocyclohexyloxyacetyldipeptide of claim 2 as the active ingredient together with common pharmaceutically acceptable carriers and adjuvants.

6. The compound of claim 2 having the formula Ia and the pharmaceuticals acceptable alkali salts thereof.

7. The composition of claim 2 having the formula Ib and the pharmaceutically acceptable alkali salts thereof.

* * * * *

UNITED STATES PATENT AND TRADEMARK OFFICE
CERTIFICATE OF CORRECTION

PATENT NO. : 5,231,216

DATED : July 27, 1993

INVENTOR(S) : S. Pecar, D. Kikelj, U. Urleb, M. Sollner, G. Marc, A. Krbavcic, V. Kotnik, B. Wraber-Herzog, A. Ihan, L. Povsic, etc.

It is certified that error appears in the above-identified patent and that said Letters Patent is hereby corrected as shown below:

On title page, item [54] and col. 1, line 4, change, "diasteredisomers" to ---diastereoisomers---.

On the cover page [Item 75] Inventors, line 8, change "Alojz Than" to ---Alojz Ihan---.

On the cover page [Item 22] Filed, change "Aug. 19, 1991" to ---Aug. 9, 1991---.

Column 32, line 27, change "and the pharmaceuticals acceptable" to ---and the pharmaceutically acceptable---.

Signed and Sealed this

Fourteenth Day of June, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.  :  5,231,216

DATED       :  July 27, 1993

INVENTOR(S) :  S. Pecar, D. Kikelj, U. Urleb, M. Sollner, G. Marc,
A. Krbavcic, V. Kotnik, B. Wraber-Herzog, A. Ihan, L. Povsic, etc.

It is certified that error appears in the above-identified patent and that said Letters Patent is hereby corrected as shown below:

On the cover page [Item 73], line 2, add the second Assignee "Lek, Tovarna Farmacectskih in Kemicnih Izdelkov, Verovskova 57, Ljubljana"

Signed and Sealed this

Nineteenth Day of July, 1994

*Attest:*

BRUCE LEHMAN

*Attesting Officer*     Commissioner of Patents and Trademarks